(12) United States Patent
Clemmons et al.

(10) Patent No.: US 10,947,285 B2
(45) Date of Patent: *Mar. 16, 2021

(54) COMPOUNDS, COMPOSITIONS AND USES THEREOF FOR IMPROVEMENT OF BONE DISORDERS

(71) Applicant: Amolyt Pharma, Ecully (FR)

(72) Inventors: David Clemmons, Chapel Hill, NC (US); Gang Xi, Cary, NC (US); Thomas Delale, Ecully (FR); Michel Julien, Lyons (FR); Thierry Abribat, St-Foy-lès-Lyon (FR)

(73) Assignee: Amolyt Pharma, Ecully (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/888,402

(22) Filed: Feb. 5, 2018

(65) Prior Publication Data

US 2018/0230191 A1    Aug. 16, 2018

Related U.S. Application Data

(60) Provisional application No. 62/455,124, filed on Feb. 6, 2017.

(51) Int. Cl.
| | | |
|---|---|---|
| *A61K 38/08* | (2019.01) | |
| *C07K 7/06* | (2006.01) | |
| *A61P 19/08* | (2006.01) | |
| *A61P 19/10* | (2006.01) | |
| *C07K 14/47* | (2006.01) | |
| *A61K 38/17* | (2006.01) | |
| *A61K 38/00* | (2006.01) | |

(52) U.S. Cl.
CPC .......... *C07K 14/4743* (2013.01); *A61K 38/08* (2013.01); *A61K 38/1754* (2013.01); *A61P 19/08* (2018.01); *A61P 19/10* (2018.01); *C07K 7/06* (2013.01); *A61K 38/00* (2013.01)

(58) Field of Classification Search
CPC ...... C07K 7/06; C07K 14/4743; A61K 38/08; A61K 38/1754; A61P 19/08
See application file for complete search history.

(56) References Cited

U.S. PATENT DOCUMENTS

| | | | |
|---|---|---|---|
| 9,220,746 B2 | 12/2015 | Clemmons et al. | |
| 2003/0165996 A1* | 9/2003 | Halkier | C07K 1/107 435/7.1 |
| 2008/0227125 A1* | 9/2008 | Argoud-Puy | C07K 14/47 435/7.92 |
| 2012/0149634 A1* | 6/2012 | Clemmons | A61K 38/10 514/4.8 |
| 2014/0100160 A1 | 4/2014 | Hwang | |
| 2015/0038435 A1* | 2/2015 | Hubalek | C07K 5/1008 514/21.6 |
| 2016/0039897 A1 | 2/2016 | Clemmons | |
| 2019/0352358 A1 | 11/2019 | Clemmons et al. | |
| 2019/0359676 A1 | 11/2019 | Delale et al. | |

FOREIGN PATENT DOCUMENTS

| | | |
|---|---|---|
| WO | WO2002024219 A1 | 3/2002 |
| WO | 2005014635 A2 | 2/2005 |
| WO | WO2006102715 A1 | 10/2006 |
| WO | WO2008019491 A1 | 2/2008 |
| WO | WO2009059011 A2 | 5/2009 |
| WO | WO2010-096125 | 8/2010 |
| WO | WO2010141811 A2 | 12/2010 |
| WO | WO2014165137 A1 | 10/2014 |
| WO | WO2018145006 A1 | 8/2018 |

OTHER PUBLICATIONS

Xi et al., J. Bone Miner. Res., 2014, vol. 29(11):2427-2438.*
Lim et al., J. Control Release. Sep. 10, 2013; 170(2): 219-225.*
S. H. Joo, Biomol. Ther., 2012, vol. 20(1):19-26.*
Lin et al., Neuro-Oncology, 2009, vol. 11(5):468-476.*
Xi et al. "The Heparin-Binding Domains of IGFBP-2 Mediate Its Inhibitory Effect on Preadipocyte Differentiation and Fat Development in Male Mice"; Endocrinology; vol. 154; No. 11; pp. 4146-4157; 2013.
Xi et al. "A unique peptide containing the heparin binding domain of IGFBP-2 increases bone mass in ovariectomized (OVX) rats"; Annual Meeting of the American Society for Bone and Mineral Research (ASBMR); Sep. 16-19, 2016; UNC School of Medicine.
Wheatcroft et al. "IGF-Binding Protein-2 Protects Against the Development of Obesity and Insulin Resistance"; Diabetes; Feb. 2007; vol. 56, No. 2; pp. 285-294.
DeMambro et al. "Gender-Specific Changes in Bone Turnover and Skeletal Architecture in igfbp-2-Null Mice"; Endocrinology; May 2008; vol. 149, No. 5; pp. 2051-2061.
Hedbacker et al. "Antidiabetic effects of IGFBP2, a Leptin-Regulated Gene"; Cell Metabolism; Jan. 6, 2010; vol. 11, No. 1; pp. 11-22.
Xi et al. "IGFBP-2 Directly Stimulates Osteoblast Differentiation"; Journal of Bone and Mineral Research; 2014; vol. 20; pp. 2427-2438.
Kawai al. The Heparin-binding Domain of IGFBP-2 Has Insulin-like Growth Factor Binding-independent Biologic Activity in the Growing Skeleton; Journal of Biological Chemistry; Apr. 22, 2011; vol. 286, No. 16; pp. 14670-14680.
Kawai et al. Supplemental Data "The Heparin-binding domain of IGFBP-2 has IGF binding-independent biologic activity in the growing skeleton"; 6 pages.
International Search report of PCT/US2018/016869; dated May 23, 2018; Blaine R. Copenheaver.

(Continued)

*Primary Examiner* — Xiaozhen Xie

(74) *Attorney, Agent, or Firm* — Knobbe Martens Olson & Bear LLP

(57) ABSTRACT

The present technology generally relates to peptides of IGFBP-2 that may be used to improve bone disorders. The present technology also generally relates to uses of such peptides in methods for preventing or treating bone disorders and to compositions for such uses.

7 Claims, 6 Drawing Sheets

Specification includes a Sequence Listing.

(56) References Cited

OTHER PUBLICATIONS

Arai et al. "Binding of Insulin-Like Growth Factor (IGF) I or II to IGF-Binding Protein-2 Enables It to Bind to Heparin and Extracellular Matrix", Endocrinology, (Nov. 1, 1996), vol. 137, No. 11, pp. 4571-4575.

Shen et al. "Insulin-Like Growth Factor (IGF) Binding Protein 2 Functions Coordinately with Receptor Protein Tyrosine Phosphatase β and the IGF-I Receptor to Regulate IGF-I-Stimulated Signaling", Mol. Cell Biol., 2012, vol. 32, No. 20, pp. 4116-4130.

Assefa et al. "Insulin-Like Growth Factor (IGF) Binding Protein-2, Independently of IGF-1, Induces GLUT-4 Translocation and Glucose Uptake in 3T3-L1 Adipocytes", Oxidative Medicine and Cellular Longevity, vol. 2017, Article ID: 3035184, 13 pages.

International Search Report of PCT/IB19/54302, dated Nov. 1, 2019, in 19 pages.

Antonetti, Da et al., Diabetic Retinopathy Seeing Beyond Glucose-Induced Microvascular bisease. Perspectives in Diabetes. Sep. 2006, vol. 55, No. 9; pp. 2401-2411;p. 2303, 1 st column, 1 st paragraph-2nd column, 3rd paragraph; p. 2407 , 1 st column, 2nd paragraph-3rd paragraph; DOI: 10.23371db05-1635.

Hoybye, C et al., The growth hormone-insulin-like growth factor axis in adult patients with Prader Willi syndrome. Growth Hormone & IGF Research. Oct. 2003, vol. 13, No. 5; pp. 269-274; abstract; p. 270, 2nd column,Sth paragraph; p. 273,1st column,4th paragraph; Table 2; DOI: 1 0.1016/S1 096-6374(03)00017-0.

Xi, G. et al., The Heparin-Binding Domains of IGFBP-2 Mediate Its Inhibitory Effect on Preadipocyte Differentiation and Fat Development in Male Mice. Endocrinology. Nov. 2013, Epub 27, Aug. 2013, vol. 154, No. 11.

Huvenne et al. "Rare Genetic Forms of Obesity: Clinical Approach and Current Treatments in 2016,"Obesity Facts, The European Journal of Obesity, Jun. 1, 2016, 158-173.

Chung "An Overview of Monogenic and Syndromic Obesities in Humans," Pediatr Blood Cancer, Jan. 2012, 58(1): 122-128.

\* cited by examiner

SEQUENCE LISTING

<160> NUMBER OF SEQ ID NOS: 113

<210> SEQ ID NO 1

```
<211> LENGTH: 13
<212> TYPE: PRT
<213> ORGANISM: Artificial Sequence
<220> FEATURE:
<223> OTHER INFORMATION: Synthesized

<400> SEQUENCE: 1

Lys His His Leu Gly Leu Glu Glu Pro Lys Lys Leu Arg
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthesized

<400> SEQUENCE: 2

His His Leu Gly Leu Glu Glu Pro Lys Lys Leu Arg
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthesized

<400> SEQUENCE: 3

His Leu Gly Leu Glu Glu Pro Lys Lys Leu Arg
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthesized

<400> SEQUENCE: 4

Leu Gly Leu Glu Glu Pro Lys Lys Leu Arg
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthesized

<400> SEQUENCE: 5

Lys His His Leu Gly Leu Glu Glu Pro Lys Lys Leu
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Synthesized

<400> SEQUENCE: 6

Lys His His Leu Gly Leu Glu Glu Pro Lys Lys
1               5                   10

<210> SEQ ID NO 7
<211> LENGTH: 8
```

<212> TYPE: PRT
<213> ORGANISM: Artificial Sequence
<220> FEATURE:
<223> OTHER INFORMATION: Synthesized

<400> SEQUENCE: 7

His Leu Gly Leu Glu Glu Pro Lys
1               5

<210> SEQ ID NO 8
<211> LENGTH: 7
<212> TYPE: PRT
<213> ORGANISM: Artificial Sequence
<220> FEATURE:
<223> OTHER INFORMATION: Synthesized

<400> SEQUENCE: 8

His Leu Gly Leu Glu Glu Pro
1               5

<210> SEQ ID NO 9
<211> LENGTH: 10
<212> TYPE: PRT
<213> ORGANISM: Artificial Sequence
<220> FEATURE:
<223> OTHER INFORMATION: Synthesized

<400> SEQUENCE: 9

His Leu Gly Leu Glu Glu Pro Lys Lys Leu
1               5                   10

<210> SEQ ID NO 10
<211> LENGTH: 9
<212> TYPE: PRT
<213> ORGANISM: Artificial Sequence
<220> FEATURE:
<223> OTHER INFORMATION: Synthesized

<400> SEQUENCE: 10

His Leu Gly Leu Glu Glu Pro Lys Lys
1               5

<210> SEQ ID NO 11
<211> LENGTH: 8
<212> TYPE: PRT
<213> ORGANISM: Artificial Sequence
<220> FEATURE:
<223> OTHER INFORMATION: Synthesized

<400> SEQUENCE: 11

Leu Gly Leu Glu Glu Pro Lys Lys
1               5

<210> SEQ ID NO 12
<211> LENGTH: 7
<212> TYPE: PRT
<213> ORGANISM: Artificial Sequence
<220> FEATURE:
<223> OTHER INFORMATION: Synthesized

<400> SEQUENCE: 12

Gly Leu Glu Glu Pro Lys Lys
1               5

<210> SEQ ID NO 13
<211> LENGTH: 7
<212> TYPE: PRT

```
<213> ORGANISM: Artificial Sequence
<220> FEATURE:
<223> OTHER INFORMATION: Synthesized

<400> SEQUENCE: 13

Leu Gly Leu Glu Glu Pro Lys
1               5

<210> SEQ ID NO 14
<211> LENGTH: 6
<212> TYPE: PRT
<213> ORGANISM: Artificial Sequence
<220> FEATURE:
<223> OTHER INFORMATION: Synthesized

<400> SEQUENCE: 14

Gly Leu Glu Glu Pro Lys
1               5

<210> SEQ ID NO 15
<211> LENGTH: 6
<212> TYPE: PRT
<213> ORGANISM: Artificial Sequence
<220> FEATURE:
<223> OTHER INFORMATION: Synthesized

<400> SEQUENCE: 15

Leu Gly Leu Glu Glu Pro
1               5

<210> SEQ ID NO 16
<211> LENGTH: 10
<212> TYPE: PRT
<213> ORGANISM: Artificial Sequence
<220> FEATURE:
<223> OTHER INFORMATION: Synthesized

<400> SEQUENCE: 16

His His Leu Gly Leu Glu Glu Pro Lys Lys
1               5                   10

<210> SEQ ID NO 17
<211> LENGTH: 9
<212> TYPE: PRT
<213> ORGANISM: Artificial Sequence
<220> FEATURE:
<223> OTHER INFORMATION: Synthesized

<400> SEQUENCE: 17

Ala Leu Gly Leu Glu Glu Pro Lys Lys
1               5

<210> SEQ ID NO 18
<211> LENGTH: 9
<212> TYPE: PRT
<213> ORGANISM: Artificial Sequence
<220> FEATURE:
<223> OTHER INFORMATION: Synthesized

<400> SEQUENCE: 18

His Ala Gly Leu Glu Glu Pro Lys Lys
1               5

<210> SEQ ID NO 19
<211> LENGTH: 9
<212> TYPE: PRT
<213> ORGANISM: Artificial Sequence
```

```
<220> FEATURE:
<223> OTHER INFORMATION: Synthesized

<400> SEQUENCE: 19

His Leu Ala Leu Glu Glu Pro Lys Lys
1               5

<210> SEQ ID NO 20
<211> LENGTH: 9
<212> TYPE: PRT
<213> ORGANISM: Artificial Sequence
<220> FEATURE:
<223> OTHER INFORMATION: Synthesized

<400> SEQUENCE: 20

His Leu Gly Ala Glu Glu Pro Lys Lys
1               5

<210> SEQ ID NO 21
<211> LENGTH: 9
<212> TYPE: PRT
<213> ORGANISM: Artificial Sequence
<220> FEATURE:
<223> OTHER INFORMATION: Synthesized

<400> SEQUENCE: 21

His Leu Gly Leu Ala Glu Pro Lys Lys
1               5

<210> SEQ ID NO 22
<211> LENGTH: 9
<212> TYPE: PRT
<213> ORGANISM: Artificial Sequence
<220> FEATURE:
<223> OTHER INFORMATION: Synthesized

<400> SEQUENCE: 22

His Leu Gly Leu Glu Ala Pro Lys Lys
1               5

<210> SEQ ID NO 23
<211> LENGTH: 9
<212> TYPE: PRT
<213> ORGANISM: Artificial Sequence
<220> FEATURE:
<223> OTHER INFORMATION: Synthesized

<400> SEQUENCE: 23

His Leu Gly Leu Glu Glu Ala Lys Lys
1               5

<210> SEQ ID NO 24
<211> LENGTH: 9
<212> TYPE: PRT
<213> ORGANISM: Artificial Sequence
<220> FEATURE:
<223> OTHER INFORMATION: Synthesized

<400> SEQUENCE: 24

His Leu Gly Leu Glu Glu Pro Ala Lys
1               5

<210> SEQ ID NO 25
<211> LENGTH: 9
<212> TYPE: PRT
<213> ORGANISM: Artificial Sequence
<220> FEATURE:
```

```
<223> OTHER INFORMATION: Synthesized

<400> SEQUENCE: 25

His Leu Gly Leu Glu Glu Pro Lys Ala
1               5

<210> SEQ ID NO 26
<211> LENGTH: 9
<212> TYPE: PRT
<213> ORGANISM: Artificial Sequence
<220> FEATURE:
<223> OTHER INFORMATION: Synthesized

<400> SEQUENCE: 26

His Leu Gly Leu Glu Arg Pro Lys Lys
1               5

<210> SEQ ID NO 27
<211> LENGTH: 9
<212> TYPE: PRT
<213> ORGANISM: Artificial Sequence
<220> FEATURE:
<223> OTHER INFORMATION: Synthesized

<400> SEQUENCE: 27

His Leu Gly Leu Glu Phe Pro Lys Lys
1               5

<210> SEQ ID NO 28
<211> LENGTH: 9
<212> TYPE: PRT
<213> ORGANISM: Artificial Sequence
<220> FEATURE:
<223> OTHER INFORMATION: Synthesized

<400> SEQUENCE: 28

His Leu Gly Leu Glu Ile Pro Lys Lys
1               5

<210> SEQ ID NO 29
<211> LENGTH: 9
<212> TYPE: PRT
<213> ORGANISM: Artificial Sequence
<220> FEATURE:
<223> OTHER INFORMATION: Synthesized

<400> SEQUENCE: 29

His Leu Gly Leu Glu Pro Pro Lys Lys
1               5

<210> SEQ ID NO 30
<211> LENGTH: 9
<212> TYPE: PRT
<213> ORGANISM: Artificial Sequence
<220> FEATURE:
<223> OTHER INFORMATION: Synthesized

<400> SEQUENCE: 30

His Leu Gly Leu Glu Ser Pro Lys Lys
1               5

<210> SEQ ID NO 31
<211> LENGTH: 9
<212> TYPE: PRT
<213> ORGANISM: Artificial Sequence
<220> FEATURE:
<223> OTHER INFORMATION: Synthesized
```

<400> SEQUENCE: 31

His Leu Gly Leu Glu Glu Arg Lys Lys
1               5

<210> SEQ ID NO 32
<211> LENGTH: 9
<212> TYPE: PRT
<213> ORGANISM: Artificial Sequence
<220> FEATURE:
<223> OTHER INFORMATION: Synthesized

<400> SEQUENCE: 32

His Leu Gly Leu Glu Glu Phe Lys Lys
1               5

<210> SEQ ID NO 33
<211> LENGTH: 9
<212> TYPE: PRT
<213> ORGANISM: Artificial Sequence
<220> FEATURE:
<223> OTHER INFORMATION: Synthesized

<400> SEQUENCE: 33

His Leu Gly Leu Glu Glu Leu Lys Lys
1               5

<210> SEQ ID NO 34
<211> LENGTH: 9
<212> TYPE: PRT
<213> ORGANISM: Artificial Sequence
<220> FEATURE:
<223> OTHER INFORMATION: Synthesized

<400> SEQUENCE: 34

His Leu Gly Leu Glu Glu Ser Lys Lys
1               5

<210> SEQ ID NO 35
<211> LENGTH: 9
<212> TYPE: PRT
<213> ORGANISM: Artificial Sequence
<220> FEATURE:
<223> OTHER INFORMATION: Synthesized

<400> SEQUENCE: 35

His Leu Gly Leu Glu Glu Asp Lys Lys
1               5

<210> SEQ ID NO 36
<211> LENGTH: 9
<212> TYPE: PRT
<213> ORGANISM: Artificial Sequence
<220> FEATURE:
<223> OTHER INFORMATION: Synthesized

<400> SEQUENCE: 36

His Leu Gly Leu Glu Glu Pro Phe Lys
1               5

<210> SEQ ID NO 37
<211> LENGTH: 9
<212> TYPE: PRT
<213> ORGANISM: Artificial Sequence
<220> FEATURE:
<223> OTHER INFORMATION: Synthesized

```
<400> SEQUENCE: 37

His Leu Gly Leu Glu Glu Pro Pro Lys
1               5

<210> SEQ ID NO 38
<211> LENGTH: 9
<212> TYPE: PRT
<213> ORGANISM: Artificial Sequence
<220> FEATURE:
<223> OTHER INFORMATION: Synthesized

<400> SEQUENCE: 38

His Leu Gly Leu Glu Glu Pro Ser Lys
1               5

<210> SEQ ID NO 39
<211> LENGTH: 9
<212> TYPE: PRT
<213> ORGANISM: Artificial Sequence
<220> FEATURE:
<223> OTHER INFORMATION: Synthesized

<400> SEQUENCE: 39

His Leu Gly Leu Glu Glu Pro Asp Lys
1               5

<210> SEQ ID NO 40
<211> LENGTH: 9
<212> TYPE: PRT
<213> ORGANISM: Artificial Sequence
<220> FEATURE:
<223> OTHER INFORMATION: Synthesized

<400> SEQUENCE: 40

His Leu Gly Leu Glu Glu Pro Lys Phe
1               5

<210> SEQ ID NO 41
<211> LENGTH: 9
<212> TYPE: PRT
<213> ORGANISM: Artificial Sequence
<220> FEATURE:
<223> OTHER INFORMATION: Synthesized

<400> SEQUENCE: 41

His Leu Gly Leu Glu Glu Pro Lys Ile
1               5

<210> SEQ ID NO 42
<211> LENGTH: 9
<212> TYPE: PRT
<213> ORGANISM: Artificial Sequence
<220> FEATURE:
<223> OTHER INFORMATION: Synthesized

<400> SEQUENCE: 42

His Leu Gly Leu Glu Glu Pro Lys Pro
1               5

<210> SEQ ID NO 43
<211> LENGTH: 9
<212> TYPE: PRT
<213> ORGANISM: Artificial Sequence
<220> FEATURE:
<223> OTHER INFORMATION: Synthesized

<400> SEQUENCE: 43
```

His Leu Gly Leu Glu Glu Pro Lys Ser
1               5

<210> SEQ ID NO 44
<211> LENGTH: 9
<212> TYPE: PRT
<213> ORGANISM: Artificial Sequence
<220> FEATURE:
<223> OTHER INFORMATION: Synthesized

<400> SEQUENCE: 44

His Leu Gly Leu Glu Glu Pro Lys Asp
1               5

<210> SEQ ID NO 45
<211> LENGTH: 9
<212> TYPE: PRT
<213> ORGANISM: Artificial Sequence
<220> FEATURE:
<223> OTHER INFORMATION: Synthesized

<400> SEQUENCE: 45

His Leu Gly Leu Glu Glu Pro Ile Lys
1               5

<210> SEQ ID NO 46
<211> LENGTH: 9
<212> TYPE: PRT
<213> ORGANISM: Artificial Sequence
<220> FEATURE:
<223> OTHER INFORMATION: Synthesized

<400> SEQUENCE: 46

His Leu Gly Leu Glu Glu Pro Val Lys
1               5

<210> SEQ ID NO 47
<211> LENGTH: 9
<212> TYPE: PRT
<213> ORGANISM: Artificial Sequence
<220> FEATURE:
<223> OTHER INFORMATION: Synthesized

<400> SEQUENCE: 47

His Leu Gly Leu Glu Glu Pro Gln Lys
1               5

<210> SEQ ID NO 48
<211> LENGTH: 9
<212> TYPE: PRT
<213> ORGANISM: Artificial Sequence
<220> FEATURE:
<223> OTHER INFORMATION: Synthesized

<400> SEQUENCE: 48

His Leu Gly Leu Glu Glu Pro Thr Lys
1               5

<210> SEQ ID NO 49
<211> LENGTH: 9
<212> TYPE: PRT
<213> ORGANISM: Artificial Sequence
<220> FEATURE:
<223> OTHER INFORMATION: Synthesized

<400> SEQUENCE: 49

His Leu Gly Leu Glu Glu Pro Glu Lys
1               5

<210> SEQ ID NO 50
<211> LENGTH: 9
<212> TYPE: PRT
<213> ORGANISM: Artificial Sequence
<220> FEATURE:
<223> OTHER INFORMATION: Synthesized

<400> SEQUENCE: 50

His Leu Gly Leu Glu Glu Pro Lys His
1               5

<210> SEQ ID NO 51
<211> LENGTH: 9
<212> TYPE: PRT
<213> ORGANISM: Artificial Sequence
<220> FEATURE:
<223> OTHER INFORMATION: Synthesized

<400> SEQUENCE: 51

His Leu Gly Leu Glu Glu Pro Lys Arg
1               5

<210> SEQ ID NO 52
<211> LENGTH: 9
<212> TYPE: PRT
<213> ORGANISM: Artificial Sequence
<220> FEATURE:
<223> OTHER INFORMATION: Synthesized

<400> SEQUENCE: 52

His Leu Gly Leu Glu Glu Pro Lys Leu
1               5

<210> SEQ ID NO 53
<211> LENGTH: 9
<212> TYPE: PRT
<213> ORGANISM: Artificial Sequence
<220> FEATURE:
<223> OTHER INFORMATION: Synthesized

<400> SEQUENCE: 53

His Leu Gly Leu Glu Glu Pro Lys Met
1               5

<210> SEQ ID NO 54
<211> LENGTH: 9
<212> TYPE: PRT
<213> ORGANISM: Artificial Sequence
<220> FEATURE:
<223> OTHER INFORMATION: Synthesized

<400> SEQUENCE: 54

His Leu Gly Leu Glu Glu Pro Lys Trp
1               5

<210> SEQ ID NO 55
<211> LENGTH: 9
<212> TYPE: PRT
<213> ORGANISM: Artificial Sequence
<220> FEATURE:
<223> OTHER INFORMATION: Synthesized

<400> SEQUENCE: 55

His Leu Gly Leu Glu Glu Pro Lys Val

```
<210> SEQ ID NO 56
<211> LENGTH: 9
<212> TYPE: PRT
<213> ORGANISM: Artificial Sequence
<220> FEATURE:
<223> OTHER INFORMATION: Synthesized

<400> SEQUENCE: 56

His Leu Gly Leu Glu Glu Pro Lys Gln
1               5

<210> SEQ ID NO 57
<211> LENGTH: 9
<212> TYPE: PRT
<213> ORGANISM: Artificial Sequence
<220> FEATURE:
<223> OTHER INFORMATION: Synthesized

<400> SEQUENCE: 57

His Leu Gly Leu Glu Glu Pro Lys Asn
1               5

<210> SEQ ID NO 58
<211> LENGTH: 9
<212> TYPE: PRT
<213> ORGANISM: Artificial Sequence
<220> FEATURE:
<223> OTHER INFORMATION: Snythesized

<400> SEQUENCE: 58

His Leu Gly Leu Glu Glu Pro Lys Tyr
1               5

<210> SEQ ID NO 59
<211> LENGTH: 9
<212> TYPE: PRT
<213> ORGANISM: Artificial Sequence
<220> FEATURE:
<223> OTHER INFORMATION: Synthesized

<400> SEQUENCE: 59

His Leu Gly Leu Glu Glu Pro Lys Thr
1               5

<210> SEQ ID NO 60
<211> LENGTH: 9
<212> TYPE: PRT
<213> ORGANISM: Artificial Sequence
<220> FEATURE:
<223> OTHER INFORMATION: Synthesized

<400> SEQUENCE: 60

His Leu Gly Leu Glu Glu Pro Lys Glu
1               5

<210> SEQ ID NO 61
<211> LENGTH: 9
<212> TYPE: PRT
<213> ORGANISM: Artificial Sequence
<220> FEATURE:
<223> OTHER INFORMATION: Snythesized

<400> SEQUENCE: 61

His Leu Gly Leu Glu Glu Pro Ser Pro
1               5
```

```
<210> SEQ ID NO 62
<211> LENGTH: 9
<212> TYPE: PRT
<213> ORGANISM: Artificial Sequence
<220> FEATURE:
<223> OTHER INFORMATION: Synthesized

<400> SEQUENCE: 62

His Leu Gly Leu Glu Glu Pro Ser Ser
1               5

<210> SEQ ID NO 63
<211> LENGTH: 13
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<220> FEATURE:
<221> NAME/KEY: MOD_RES
<222> LOCATION: (1)..(1)
<223> OTHER INFORMATION: Pegylated

<400> SEQUENCE: 63

Lys His His Leu Gly Leu Glu Glu Pro Lys Lys Leu Arg
1               5                   10

<210> SEQ ID NO 64
<211> LENGTH: 13
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (13)..(13)
<223> OTHER INFORMATION: Pegylated

<400> SEQUENCE: 64

Lys His His Leu Gly Leu Glu Glu Pro Lys Lys Leu Arg
1               5                   10

<210> SEQ ID NO 65
<211> LENGTH: 10
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: Pegylated

<400> SEQUENCE: 65

His His Leu Gly Leu Glu Glu Pro Lys Lys
1               5                   10

<210> SEQ ID NO 66
<211> LENGTH: 10
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (10)..(10)
<223> OTHER INFORMATION: Pegylated
```

```
<400> SEQUENCE: 66

His His Leu Gly Leu Glu Glu Pro Lys Lys
1               5                   10

<210> SEQ ID NO 67
<211> LENGTH: 9
<212> TYPE: PRT
<213> ORGANISM: Artificial Sequence
<220> FEATURE:
<223> OTHER INFORMATION: Snythesized
<220> FEATURE:
<221> NAME/KEY: MOD_RES
<222> LOCATION: (1)..(1)
<223> OTHER INFORMATION: Pegylated

<400> SEQUENCE: 67

His Leu Gly Leu Glu Glu Pro Lys Lys
1               5

<210> SEQ ID NO 68
<211> LENGTH: 10
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: Acylated with C16:0

<400> SEQUENCE: 68

His His Leu Gly Leu Glu Glu Pro Lys Lys
1               5                   10

<210> SEQ ID NO 69
<211> LENGTH: 10
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: Acylated with C18:0

<400> SEQUENCE: 69

His His Leu Gly Leu Glu Glu Pro Lys Lys
1               5                   10

<210> SEQ ID NO 70
<211> LENGTH: 10
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: Acylated with C20:0

<400> SEQUENCE: 70

His His Leu Gly Leu Glu Glu Pro Lys Lys
1               5                   10

<210> SEQ ID NO 71
<211> LENGTH: 9
<212> TYPE: PRT
<213> ORGANISM: Artificial Sequence
```

-continued

```
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: Acylated with C14:0

<400> SEQUENCE: 71

His Leu Gly Leu Glu Glu Pro Lys Lys
1               5

<210> SEQ ID NO 72
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: Acylated with C16:0

<400> SEQUENCE: 72

His Leu Gly Leu Glu Glu Pro Lys Lys
1               5

<210> SEQ ID NO 73
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: Acylated with C18:0

<400> SEQUENCE: 73

His Leu Gly Leu Glu Glu Pro Lys Lys
1               5

<210> SEQ ID NO 74
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: Acylated with C20:0

<400> SEQUENCE: 74

His Leu Gly Leu Glu Glu Pro Lys Lys
1               5

<210> SEQ ID NO 75
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: Di-acylated with C16:0

<400> SEQUENCE: 75

His Leu Gly Leu Glu Glu Pro Lys Lys
1               5
```

```
<210> SEQ ID NO 76
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (9)..(9)
<223> OTHER INFORMATION: Acylated with C16:0

<400> SEQUENCE: 76

His Leu Gly Leu Glu Glu Pro Lys Lys
1               5

<210> SEQ ID NO 77
<211> LENGTH: 9
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (1)..(9)
<223> OTHER INFORMATION: Cyclic peptide

<400> SEQUENCE: 77

His Leu Gly Leu Glu Glu Pro Lys Lys
1               5

<210> SEQ ID NO 78
<211> LENGTH: 13
<212> TYPE: PRT
<213> ORGANISM: Artificial Sequence
<220> FEATURE:
<223> OTHER INFORMATION: Synthesized
<220> FEATURE:
<221> NAME/KEY: MOD_RES
<222> LOCATION: (1)..(1)
<223> OTHER INFORMATION: Acylated with C16:0

<400> SEQUENCE: 78

Lys His His Leu Gly Leu Glu Glu Pro Lys Lys Leu Arg
1               5                   10

<210> SEQ ID NO 79
<211> LENGTH: 6
<212> TYPE: PRT
<213> ORGANISM: Artificial Sequence
<220> FEATURE:
<223> OTHER INFORMATION: Synthesized

<400> SEQUENCE: 79

Gly Leu Glu Glu Pro Leu
1               5

<210> SEQ ID NO 80
<211> LENGTH: 6
<212> TYPE: PRT
<213> ORGANISM: Artificial Sequence
<220> FEATURE:
<223> OTHER INFORMATION: Synthesized

<400> SEQUENCE: 80

Gly Leu Glu Glu Pro Arg
1               5
```

```
<210> SEQ ID NO 81
<211> LENGTH: 6
<212> TYPE: PRT
<213> ORGANISM: Artificial Sequence
<220> FEATURE:
<223> OTHER INFORMATION: Snythesized

<400> SEQUENCE: 81

Gly Leu Asp Glu Pro Lys
1               5

<210> SEQ ID NO 82
<211> LENGTH: 6
<212> TYPE: PRT
<213> ORGANISM: Artificial Sequence
<220> FEATURE:
<223> OTHER INFORMATION: Synthesized

<400> SEQUENCE: 82

Gly Leu Glu Asp Pro Lys
1               5

<210> SEQ ID NO 83
<211> LENGTH: 6
<212> TYPE: PRT
<213> ORGANISM: Artificial Sequence
<220> FEATURE:
<223> OTHER INFORMATION: Synthesized

<400> SEQUENCE: 83

Gly Gly Glu Glu Pro Lys
1               5

<210> SEQ ID NO 84
<211> LENGTH: 6
<212> TYPE: PRT
<213> ORGANISM: Artificial Sequence
<220> FEATURE:
<223> OTHER INFORMATION: Synthesized

<400> SEQUENCE: 84

Gly Val Glu Glu Pro Lys
1               5

<210> SEQ ID NO 85
<211> LENGTH: 6
<212> TYPE: PRT
<213> ORGANISM: Artificial Sequence
<220> FEATURE:
<223> OTHER INFORMATION: Synthesized

<400> SEQUENCE: 85

Gly Ile Glu Glu Pro Lys
1               5

<210> SEQ ID NO 86
<211> LENGTH: 6
<212> TYPE: PRT
<213> ORGANISM: Artificial Sequence
<220> FEATURE:
<223> OTHER INFORMATION: Synthesized

<400> SEQUENCE: 86

Val Leu Glu Glu Pro Lys
1               5

<210> SEQ ID NO 87
```

```
<211> LENGTH: 6
<212> TYPE: PRT
<213> ORGANISM: Artificial Sequence
<220> FEATURE:
<223> OTHER INFORMATION: Synthesized

<400> SEQUENCE: 87

Leu Leu Glu Glu Pro Lys
1               5

<210> SEQ ID NO 88
<211> LENGTH: 6
<212> TYPE: PRT
<213> ORGANISM: Artificial Sequence
<220> FEATURE:
<223> OTHER INFORMATION: Synthesized

<400> SEQUENCE: 88

Ile Leu Glu Glu Pro Lys
1               5

<210> SEQ ID NO 89
<211> LENGTH: 9
<212> TYPE: PRT
<213> ORGANISM: Artificial Sequence
<220> FEATURE:
<223> OTHER INFORMATION: Synthesized

<400> SEQUENCE: 89

Lys Leu Gly Leu Glu Glu Pro Lys Lys
1               5

<210> SEQ ID NO 90
<211> LENGTH: 9
<212> TYPE: PRT
<213> ORGANISM: Artificial Sequence
<220> FEATURE:
<223> OTHER INFORMATION: Synthesized

<400> SEQUENCE: 90

His Val Gly Leu Glu Glu Pro Lys Lys
1               5

<210> SEQ ID NO 91
<211> LENGTH: 9
<212> TYPE: PRT
<213> ORGANISM: Artificial Sequence
<220> FEATURE:
<223> OTHER INFORMATION: Synthesized

<400> SEQUENCE: 91

His Leu Pro Leu Glu Glu Pro Lys Lys
1               5

<210> SEQ ID NO 92
<211> LENGTH: 9
<212> TYPE: PRT
<213> ORGANISM: Artificial Sequence
<220> FEATURE:
<223> OTHER INFORMATION: Synthesized

<400> SEQUENCE: 92

His Leu Gly Ile Glu Glu Pro Lys Lys
1               5

<210> SEQ ID NO 93
<211> LENGTH: 9
```

-continued

```
<212> TYPE: PRT
<213> ORGANISM: Artificial Sequence
<220> FEATURE:
<223> OTHER INFORMATION: Synthesized

<400> SEQUENCE: 93

Asn Leu Gly Leu Glu Glu Pro Lys Lys
1               5

<210> SEQ ID NO 94
<211> LENGTH: 9
<212> TYPE: PRT
<213> ORGANISM: Artificial Sequence
<220> FEATURE:
<223> OTHER INFORMATION: Synthesized

<400> SEQUENCE: 94

His Thr Gly Leu Glu Glu Pro Lys Lys
1               5

<210> SEQ ID NO 95
<211> LENGTH: 9
<212> TYPE: PRT
<213> ORGANISM: Artificial Sequence
<220> FEATURE:
<223> OTHER INFORMATION: Synthesized

<400> SEQUENCE: 95

His Leu Lys Leu Glu Glu Pro Lys Lys
1               5

<210> SEQ ID NO 96
<211> LENGTH: 9
<212> TYPE: PRT
<213> ORGANISM: Artificial Sequence
<220> FEATURE:
<223> OTHER INFORMATION: Synthesized

<400> SEQUENCE: 96

His Leu Gly Ser Glu Glu Pro Lys Lys
1               5

<210> SEQ ID NO 97
<211> LENGTH: 9
<212> TYPE: PRT
<213> ORGANISM: Artificial Sequence
<220> FEATURE:
<223> OTHER INFORMATION: Synthesized

<400> SEQUENCE: 97

His Leu Gly Leu Glu Glu Pro Tyr Lys
1               5

<210> SEQ ID NO 98
<211> LENGTH: 9
<212> TYPE: PRT
<213> ORGANISM: Artificial Sequence
<220> FEATURE:
<223> OTHER INFORMATION: Synthesized

<400> SEQUENCE: 98

His Leu Gly Leu Glu Glu Pro Gln Lys
1               5

<210> SEQ ID NO 99
<211> LENGTH: 9
<212> TYPE: PRT
```

<213> ORGANISM: Artificial Sequence
<220> FEATURE:
<223> OTHER INFORMATION: Synthesized

<400> SEQUENCE: 99

His Leu Gly Leu Glu Glu Pro Asn Lys
1               5

<210> SEQ ID NO 100
<211> LENGTH: 9
<212> TYPE: PRT
<213> ORGANISM: Artificial Sequence
<220> FEATURE:
<223> OTHER INFORMATION: Synthesized

<400> SEQUENCE: 100

His Leu Gly Leu Glu Glu Pro Ser Phe
1               5

<210> SEQ ID NO 101
<211> LENGTH: 9
<212> TYPE: PRT
<213> ORGANISM: Artificial Sequence
<220> FEATURE:
<223> OTHER INFORMATION: Synthesized

<400> SEQUENCE: 101

His Leu Gly Leu Glu Glu Pro Ser Val
1               5

<210> SEQ ID NO 102
<211> LENGTH: 9
<212> TYPE: PRT
<213> ORGANISM: Artificial Sequence
<220> FEATURE:
<223> OTHER INFORMATION: Synthesized

<400> SEQUENCE: 102

His Leu Gly Leu Glu Glu Pro Leu Met
1               5

<210> SEQ ID NO 103
<211> LENGTH: 9
<212> TYPE: PRT
<213> ORGANISM: Artificial Sequence
<220> FEATURE:
<223> OTHER INFORMATION: Synthesized

<400> SEQUENCE: 103

His Leu Gly Leu Glu Glu Pro Leu Tyr
1               5

<210> SEQ ID NO 104
<211> LENGTH: 9
<212> TYPE: PRT
<213> ORGANISM: Artificial Sequence
<220> FEATURE:
<223> OTHER INFORMATION: Synthesized

<400> SEQUENCE: 104

His Leu Gly Leu Glu Glu Pro Leu Asn
1               5

<210> SEQ ID NO 105
<211> LENGTH: 9
<212> TYPE: PRT
<213> ORGANISM: Artificial Sequence
<220> FEATURE:
<223> OTHER INFORMATION: Synthesized

<400> SEQUENCE: 105

His Leu Gly Leu Glu Glu Pro Leu Gln
1               5

<210> SEQ ID NO 106
<211> LENGTH: 9
<212> TYPE: PRT
<213> ORGANISM: Artificial Sequence
<220> FEATURE:
<223> OTHER INFORMATION: Synthesized

<400> SEQUENCE: 106

His Leu Gly Leu Glu Glu Pro Phe Val
1               5

<210> SEQ ID NO 107
<211> LENGTH: 9
<212> TYPE: PRT
<213> ORGANISM: Artificial Sequence
<220> FEATURE:
<223> OTHER INFORMATION: Synthesized

<400> SEQUENCE: 107

His Leu Gly Leu Glu Glu Pro Phe Gln
1               5

<210> SEQ ID NO 108
<211> LENGTH: 9
<212> TYPE: PRT
<213> ORGANISM: Artificial Sequence
<220> FEATURE:
<223> OTHER INFORMATION: Synthesized

<400> SEQUENCE: 108

His Leu Gly Leu Glu Glu Pro Phe Asn
1               5

<210> SEQ ID NO 109
<211> LENGTH: 9
<212> TYPE: PRT
<213> ORGANISM: Artificial Sequence
<220> FEATURE:
<223> OTHER INFORMATION: Synthesized

<400> SEQUENCE: 109

His Leu Gly Leu Glu Glu Pro Val Met
1               5

<210> SEQ ID NO 110
<211> LENGTH: 9
<212> TYPE: PRT
<213> ORGANISM: Artificial Sequence
<220> FEATURE:
<223> OTHER INFORMATION: Synthesized

<400> SEQUENCE: 110

His Leu Gly Leu Glu Glu Pro Val Asn
1               5

<210> SEQ ID NO 111
<211> LENGTH: 9
<212> TYPE: PRT
<213> ORGANISM: Artificial Sequence
<220> FEATURE:

```
<223> OTHER INFORMATION: Synthesized

<400> SEQUENCE: 111

His Leu Gly Leu Glu Glu Pro Met Lys
1               5

<210> SEQ ID NO 112
<211> LENGTH: 8
<212> TYPE: PRT
<213> ORGANISM: Artificial Sequence
<220> FEATURE:
<223> OTHER INFORMATION: Synthesized

<400> SEQUENCE: 112

His Leu Gly Leu Glu Glu Pro Arg
1               5

<210> SEQ ID NO 113
<211> LENGTH: 8
<212> TYPE: PRT
<213> ORGANISM: Artificial Sequence
<220> FEATURE:
<223> OTHER INFORMATION: Synthesized

<400> SEQUENCE: 113

His Leu Gly Leu Glu Glu Pro His
1               5
```

COMPOUNDS, COMPOSITIONS AND USES THEREOF FOR IMPROVEMENT OF BONE DISORDERS

CROSS-REFERENCE TO RELATED APPLICATION

The present application claims priority to and benefit from U.S. Provisional Patent Application 62/455,124, filed on Feb. 6, 2017, the disclosure of which is incorporated herein by reference in its entirety.

INCORPORATION BY REFERENCE OF MATERIAL IN ASCII TEXT FILE

This application incorporates by reference the Sequence Listing contained in the following ASCII text file being submitted on May 12, 2020: File Name: BCF002_001AUS_ST25.txt; created May 11, 2020, 22.6 KB in size.

FIELD OF TECHNOLOGY

The present technology generally relates to compounds, in particular peptides that may be used to improve bone disorders. The present technology also generally relates to uses of such compounds in methods for preventing and/or treating bone disorders and to compositions for such uses.

BACKGROUND INFORMATION

Insulin-like growth factor binding protein-2 (IGFBP-2) is a 36,000 Dalton protein that is a member of the IGFBP family. There are six (6) forms of high affinity IGF binding proteins. In addition to binding the insulin-like growth factors I and II and acting as transport proteins, these proteins have been shown to have some actions that are independent of their ability to bind to IGFs.

IGFBP-2 is the second most abundant binding protein in serum. It circulates in concentrations in humans that vary between 100-600 ng/ml. Protein concentrations are high during fetal life and at birth and fall progressively during childhood and adolescence. There is a slight rise, an approximately 25% increase that occurs between 60-80 years of age. Serum concentrations of IGFBP-2 are regulated by hormones and nutrients. Fasting causes a significant increase in IGFBP-2 and feeding (particularly feeding protein) restores concentrations to normal. Concentrations are also suppressed by administration of insulin or growth hormone, and are increased by insulin-like growth factor-I. This is due in part to suppression of growth hormone and insulin, both of which are suppressed by administering IGF-I.

In addition to its role as a carrier protein for Insulin-like growth factors, IGFBP-2 controls bone mass and fat metabolism. IGFBP-2 knockout mice (IGFBP-2-/-) have reduced bone mass and increased fat mass (DeMambro, Endocrinology, 2008). In contrast, overexpression of IGFBP-2 in mice led to reduced susceptibility to diet-induced obesity and improved insulin sensitivity (Wheatcroft, Diabetes, 2007; Hedbacker, Cell Metab, 2010). In vitro, IGFBP-2 directly stimulates murine and human osteoblast differentiation (Xi, JBMR, 2014) and in contrast inhibits preadipocyte differentiation (Wheatcroft, Diabetes, 2007).

As others IGFBPs, the N-terminal region of IGFBP-2 contains an IGF-I binding site, whereas the C-terminal region facilitates IGF-I binding and accounts for the ability to bind to extracellular matrix. IGFBP-2 also comprises two heparin binding domains (HBD) that confer IGF-binding independent functions. HBD1 is a unique HBD that is located in the linker region whereas HBD2 is located in the C-terminal region. While both HBD1 and HBD2 account for the IGFBP-2 ability to inhibit adipogenesis (Xi, Endocrinology, 2013), only HBD1 mediates properties on bone mass acquisition and osteoblast differentiation (Kawai, J B C, 2011; Xi, JBMR, 2014).

Prior studies have disclosed peptides including HBD. For example, WO 2005/014635, which is incorporated herein by reference, discloses Cardiovascular disorder Plasma Polypeptides (CPPs) sharing amino acid sequence similarities with HBD1. WO 2005/014635 suggests a potential diagnostic function for such CPPs. U.S. Pat. No. 9,220,746, which is also incorporated herein by reference, discloses certain HBD1 peptides which conserve the osteoblastogenesis activity of IGFBP-2. U.S. Pat. No. 9,220,746, proposes a role for these peptide in the treatment of bone-related conditions.

The size of a peptide influences its efficiency as a therapeutic agent. Longer peptides are usually rapidly degraded following administration and their in vivo efficacy is often weak following intravenous, subcutaneous or intramuscular bolus administration. In addition, manufacturing long peptide is an extensive and expensive process, whether it is manufactured by solid-phase peptide synthesis or by recombinant technology. Finally, chronically treating patients with a long peptide might represent safety risks for the patients in the form of immunogenicity. Raising neutralizing antibodies against a natural peptide is a potential major health risk for the patients. As such, it is highly desirable to obtain shorter fragments which retain the activity of the full length peptide and avoid the drawbacks of longer peptides.

In view of the above, it would be highly desirable to identify even smaller size peptides of HBD1 that would possess a comparable biological activity to the full-length HBD1 but that would be easier and less costly to manufacture.

SUMMARY OF DISCLOSED TECHNOLOGY

The present technology proposes fragments of IGFBP-2, in particular fragments of HBD1, that retain the activity of the full-length HBD1 and that may be useful in prevention or treatment of bone disorders.

According to various aspects, the present technology relates to an isolated peptide comprising a fragment of heparin binding domain (HBD) as set forth in SEQ ID NO: 1, said fragment being 6 to 9 amino acids in length and comprising an amino acid sequence GLEEPK as set forth in SEQ ID NO: 14 or an analog thereof.

According to various aspects, the present technology relates to an isolated peptide comprising a fragment of the heparin binding domain (HBD), wherein the HBD has the amino acid sequence KHHLGLEEPKKLR (SEQ ID NO: 1), said fragment being 6 to 9 amino acids in length and comprising an amino acid sequence GLEEPK (SEQ ID NO: 14) or an analog thereof.

According to various aspects, the present technology relates to an isolated peptide consisting of a fragment of heparin binding domain (HBD) as set forth in SEQ ID NO: 1, said fragment being 6 to 9 amino acids in length and comprising an amino acid sequence GLEEPK as set forth in SEQ ID NO: 14 or an analog thereof.

According to various aspects, the present technology relates to an isolated peptide consisting of a fragment of heparin binding domain (HBD) as set forth in SEQ ID NO: 1, said fragment being 6 to 10 amino acids in length and comprising an amino acid sequence GLEEPK as set forth in SEQ ID NO: 14 or an analog thereof for use in prevention or treatment of a bone disorder.

According to various aspects, the present technology relates to the use of the isolated peptides as defined herein for prevention and/or treatment of a bone disorder in a subject in need thereof.

According to various aspects, the present technology relates to the use of the isolated peptides as defined herein in the manufacture of a medicament for prevention and/or treatment of a bone disorder in a subject in need thereof.

According to various aspects, the present technology relates to the use of the isolated peptides as defined herein for enhancement of bone formation in a subject in need thereof.

According to various aspects, the present technology relates to the use of the isolated peptides as defined herein in the manufacture of a medicament for enhancement of bone formation in a subject in need thereof.

According to various aspects, the present technology relates to the use of the isolated peptides as defined herein for inhibiting bone resorption in a subject in need thereof.

According to various aspects, the present technology relates to the use of the isolated peptides as defined herein in the manufacture of a medicament for inhibiting bone resorption in a subject in need thereof.

According to various aspects, the present technology relates to the use of the isolated peptides as defined herein for inducing deposition of bone in a subject in need thereof.

According to various aspects, the present technology relates to the use of the isolated peptides as defined herein in the manufacture of a medicament for inducing deposition of bone in a subject in need thereof.

According to various aspects, the present technology relates to the use of the isolated peptides as defined herein for inducing maturation of bone in a subject in need thereof.

According to various aspects, the present technology relates to the use of the isolated peptides as defined herein in the manufacture of a medicament for inducing maturation of bone in a subject in need thereof.

According to various aspects, the present technology relates to the use of the isolated peptides as defined herein to stimulate osteoblastogenesis in a subject in need thereof.

According to various aspects, the present technology relates to a method for prevention and/or treatment of a bone disorder in a subject in need thereof, the method comprising administering an isolated peptide as defined herein to a subject in an amount effective to prevent or treat the bone disorder in the subject.

According to various aspects, the present technology relates to a method for enhancing bone formation in a subject in need thereof, the method comprising administering an isolated peptide as defined herein to the subject in an amount effective to prevent or enhance bone formation in the subject.

According to various aspects, the present technology relates to a method for inhibiting bone resorption in a subject in need thereof, the method comprising administering an isolated peptide as defined herein to the subject in an amount effective to inhibit bone resorption in the subject.

According to various aspects, the present technology relates to a method for inducing deposition of bone in a subject in need thereof, the method comprising administering an isolated peptide as defined herein to the subject in an amount effective to induce bone deposition in the subject.

According to various aspects, the present technology relates to a method for inducing maturation of bone in a subject in need thereof, the method comprising administering an isolated peptide as defined herein to the subject in an amount effective to induce maturation of bone in the subject.

According to various aspects, the present technology relates to a method of expanding stem cells in vitro or ex vivo, comprising contacting an isolated peptide as defined herein with stem cells from a subject, wherein said stem cells are maintained under conditions whereby they are reintroduced into the subject.

According to various aspects, the present technology relates to a pharmaceutical composition comprising one or more isolated peptide as defined herein in combination with a pharmaceutically acceptable carrier.

According to various aspects, the present technology relates to the use of an isolated peptide as defined herein for inhibition of fat cell differentiation in the subject.

According to various aspects, the present technology relates to the use of an isolated peptide as defined herein in the manufacture of a medicament for inhibition of fat cell differentiation in a subject.

According to various aspects, the present technology relates to the use of an isolated peptide as defined herein for modulation of fat mass in a subject.

According to various aspects, the present technology relates to the use of an isolated peptide as defined herein in the manufacture of a medicament for modulation of fat mass in a subject.

Other aspects and features of the present technology will become apparent to those ordinarily skilled in the art upon review of the following description of specific embodiments in conjunction with the accompanying drawings.

BRIEF DESCRIPTION OF DRAWINGS

All features of embodiments which are described in this disclosure are not mutually exclusive and can be combined with one another. For example, elements of one embodiment can be utilized in the other embodiments without further mention. A detailed description of specific embodiments is provided herein below with reference to the accompanying drawings in which:

FIG. 5A shows BV/TV; FIG. 5B shows Tb.N; FIG. 5C shows Conc. D (*: p-value<0.05, : p-value<0.01, *: p-value<0.001 vs OVX vehicle)

DETAILED DESCRIPTION OF TECHNOLOGY

Figure 1:
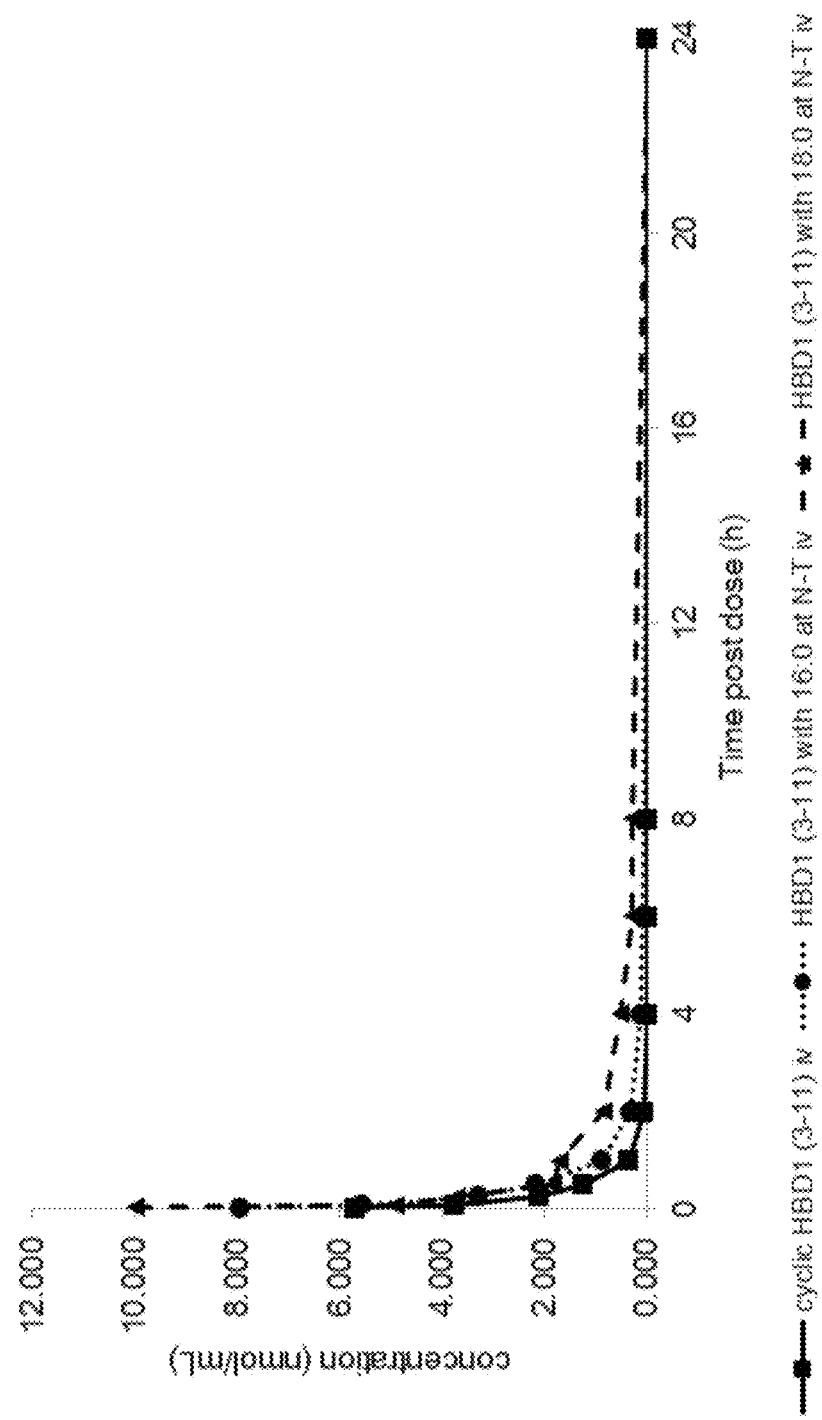
FIG. 1 is a graph showing the pharmacokinetic profile of peptides according to some embodiments of the present technology in male Sprague Dawley rats after intravenous injection of cyclic HBD1 (3-11), HBD1 (3-11) with C16:0 at N-terminal, HBD1 (3-11) with C18:0 at N-terminal.

This present description of the technology is not intended to be a detailed catalog of all the different ways in which the present technology may be implemented, or all the features that may be added to the present technology. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which does not depart from the present technology. Hence, the following specification is intended to illustrate some particular embodiments of the present technology, and not to exhaustively specify all permutations, combinations and variations thereof. Unless defined otherwise, all technical and scientific terms used herein have the same meaning as commonly understood by one of skill in the art to which the present technology belongs.

The present disclosure stems from the work performed by the present discoverers on peptide fragments of IGFBP-2, in particular on peptide fragments of the heparin binding domain (HBD) of IGFBP-2, and on their study of how these peptide fragments can be used in methods of improving bones, such as in methods of preventing and/or treatment bone disorders.

A. Compounds, Peptides, Fragments and Analogs Thereof

As used herein, the expression and term "heparin binding domain" and "HBD" refer to the heparin binding domain of IGFBP-2. The term "HBD1" refers to the heparin binding domain 1 of IGFBP-2. HBD1 is intended to refer to a peptide having the amino acid sequence as set forth in SEQ ID NO: 1, namely: $^1$-KHHLGLEEPKKLR-$^{13}$, wherein "$^1$" refers to amino acid residue at the 5'-end or N-Terminal of this HBD1 peptide and "$^{13}$" refers to amino acid residue at the 3'-end or C-Terminal of this HBD1 peptide. Accordingly, the amino acids of HBD1 occupy the following positions:

Well recognized abbreviations in the art will be used to describe amino acids, including levorotatory amino acids (L-amino acids or L or L-form) and dextrorotary amino acids (D-amino acids or D or D-form), Alanine (Ala or A), Arginine (Arg or R), Asparagine (Asn or N), Aspartic acid (Asp or D), Cysteine (Cys or C), Glutamic acid (Glu or E), Glutamine (Gln or Q), Glycine (Gly or G), Histidine (His or H), Isoleucine (Ile or I), Leucine (Leu or L), Lysine (Lys or K), Methionine (Met or M), Phenylalanine (Phe or F), Proline (Pro or P), Serine (Ser or S), Threonine (Thr or T), Tryptophan (Trp or W), Tyrosine (Tyr or Y) and Valine (Val or V). An L-amino acid residue within the native peptide sequence may be altered to any one of the 20 L-amino acids commonly found in proteins or any one of the corresponding D-amino acids, rare amino acids, such as, but not limited to, 4-hydroxyproline or hydroxylysine, or a non-protein amino acid, such as P-alanine or homoserine. Unless otherwise indicated, an amino acid named herein refers to the L-form.

Naturally-occurring variations of the peptides defined herein are those that may comprise substitutions, additions or deletions of one or more amino acids which result due to discrete changes in the nucleotide sequence of the encoding gene or alleles thereof or which result due to alternative splicing of the transcribed RNA. It is understood that these changes do not substantially affect the properties, pharmacological and biological characteristics of the peptide variants.

The peptides of the present disclosure may be in the form of salts. Particularly the acidic functions of the molecule may be replaced by a salt derivative thereof such as, but not limited to, a trifluoroacetate salt.

By "peptide", "polypeptide" or "protein" is meant any chain of amino acids, regardless of length or post-translational modification (e.g., glycosylation or phosphorylation), or chemical modification, or those containing unnatural or unusual amino acids such as D-Tyr, ornithine, amino-adipic acid.

In some embodiments, the peptide of the present disclosure comprises a fragment of HBD1. In some embodiments, the peptide is 10 amino acids in length. In some embodiments, the peptide is 9 amino acids in length. In some other embodiments, the peptide is 8 amino acids in length. In some other embodiments, the peptide is 7 amino acids in length. In some other embodiments, the peptide is 6 amino acids in length. In some embodiments, the peptide is 5 amino acids in length.

As used herein, the term and expression "fragment" or "fragment thereof" refer to an amino acid fragment of a peptide such as IGFBP-2 or of the HBD of IGFBP-2 or of the HBD1 of IGFBP-2. Fragments of HBD1 are shorter than 13 amino acid residues. Fragments of HBD1 may therefore be 12, 11, 10, 9, 8, 7, 6, 5 or 4 amino acid residues in length. In some embodiments, the fragment of HBD1 is 10 amino acids in length. In some embodiments, the fragment of HBD1 is 9 amino acids in length. In some other embodiments, the fragment of HBD1 is 8 amino acids in length. In some other embodiments, the fragment of HBD1 is 7 amino acids in length. In some other embodiments, the fragment of HBD1 is 6 amino acids in length. In some other embodiments, the fragment of HBD1 is 5 amino acids in length. In some other embodiments, the fragment of HBD1 is 4 amino acids in length.

In one embodiment, the present disclosure provides peptides having the amino acid sequences depicted in Table 1. HBD1 (1-13) represents the full-length HBD1. The remaining peptides presented in Table 1 are fragments of HBD1 (1-13), wherein amino acid residues at the N-terminal or at the C-terminal or at both the N-terminal and the C-terminal are absent.

TABLE 1

Examples of fragments of HBD1

| SEQ ID NOs | Fragment Surname | Amino Acid Sequence | Number of Amino acid residues |
|---|---|---|---|
| SEQ ID NO: 1 | HBD1 (1-13) | $^1$-KHHLGLEEPKKLR-$^{13}$ | 13 |
| SEQ ID NO: 2 | HBD1 (2-13) | $^1$-_HHLGLEEPKKLR-$^{13}$ | 12 |
| SEQ ID NO: 3 | HBD1 (3-13) | $^1$-__HLGLEEPKKLR-$^{13}$ | 11 |
| SEQ ID NO: 4 | HBD1 (4-13) | $^1$-___LGLEEPKKLR-$^{13}$ | 10 |
| SEQ ID NO: 5 | HBD1 (1-12) | $^1$-KHHLGLEEPKKL_-$^{13}$ | 12 |
| SEQ ID NO: 6 | HBD1 (1-11) | $^1$-KHHLGLEEPKK__-$^{13}$ | 11 |
| SEQ ID NO: 7 | HBD1 (3-10) | $^1$-__HLGLEEPK___-$^{13}$ | 8 |
| SEQ ID NO: 8 | HBD1 (3-9) | $^1$-__HLGLEEP____-$^{13}$ | 7 |
| SEQ ID NO: 9 | HBD1 (3-12) | $^1$-__HLGLEEPKKL_-$^{13}$ | 10 |
| SEQ ID NO: 10 | HBD1 (3-11) | $^1$-__HLGLEEPKK__-$^{13}$ | 9 |
| SEQ ID NO: 11 | HBD1 (4-11) | $^1$-___LGLEEPKK__-$^{13}$ | 8 |
| SEQ ID NO: 12 | HBD1 (5-11) | $^1$____GLEEPKK__-$^{13}$ | 7 |
| SEQ ID NO: 13 | HBD1 (4-10) | $^1$-___LGLEEPK___-$^{13}$ | 7 |
| SEQ ID NO: 14 | HBD1 (5-10) | $^1$-____GLEEPK___-$^{13}$ | 6 |
| SEQ ID NO: 15 | HBD1 (4-9) | $^1$-___LGLEEP____-$^{13}$ | 6 |
| SEQ ID NO: 16 | HBD1 (2-11) | $^1$-_HHLGLEEPKK__-$^{13}$ | 10 |
| SEQ ID NO: 77 | HBD1 (3-11) cyclic | $^{cyclic1}$-HLGLEEPKK-$^{13cycle}$ | 9 |
| SEQ ID NO: 114 | HBD1 (5-9) | | 5 |
| SEQ ID NO: 115 | HBD1 (3-9) | $^1$-__X$_1$X$_2$GLEEPX$_8$X$_9$__-$^{13}$ | 5 to 9 |

In some embodiments, the peptides of the present disclosure are "purified", "isolated" or "substantially pure". The peptides are "purified", "isolated" or "substantially pure" when they are separated from the components that naturally accompany them. Typically, a compound is substantially pure when it is at least about 60%, about 65%, about 70%, about 75%, about 80%, about 85%, about 90%, about 91%, about 92%, about 93%, about 94%, about 95%, about 96%, about 97%, about 98%, or about 99%, by weight, of the total material in a sample. Techniques for purifying or isolating peptides are commonly known and used in the art and will be known to persons skilled in the art.

In some other embodiments, certain peptides according to the present disclosure may also be in cyclized form, such that the N- or C-termini are linked head-to-tail either directly, or through the insertion of a linker moiety, such moiety itself generally comprises one or more amino acid residues as required to join the backbone in such a manner as to avoid altering the three-dimensional structure of the peptide with respect to the non-cyclized form. Such peptide derivatives may have improved stability and bioavailability relative to the non-cyclized peptides.

Methods for cyclizing peptides are well known in the art. Cyclisation may be accomplished by disulfide bond formation between two side chain functional groups, amide or ester bond formation between one side chain functional group and the backbone α-amino or carboxyl function, amide or ester bond formation between two side chain functional groups, or amide bond formation between the backbone α-amino and carboxyl functions. These cyclisation reactions have been traditionally carried out at high dilution in solution. Cyclisation is commonly accomplished while the peptide is attached to the resin. One of the most common ways of synthesizing cyclic peptides on a solid support is by attaching the side chain of an amino acid to the resin. Using appropriate protection strategies, the C- and N-termini can be selectively deprotected and cyclized on the resin after chain assembly. This strategy is widely used, and is compatible with either tert-butyloxycarbonyl (Boc) or 9-fluorenylmethoxycarbonyl (Fmoc) protocols. However, it is restricted to peptides that contain appropriate side chain functionality to attach to the solid support. A number of approaches may be used to achieve efficient synthesis of cyclic peptides. One procedure for synthesizing cyclic peptides is based on cyclisation with simultaneous cleavage from the resin. After an appropriate peptide sequence is assembled by solid phase synthesis on the resin or a linear sequence is appended to resin, the deprotected amino group can react with its anchoring active linkage to produce protected cyclic peptides. In general, a final deprotection step is required to yield the target cyclic peptide. The procedures for synthesizing cyclic peptides are well known in the art.

In other embodiments, the present disclosure provides analogs of the peptides defined herein. As used herein, the term "analog" refers to a peptide that has the physiological activity of the parent compound thereof, and that includes one or more (e.g., two, three, four, five or six or more) amino acids different from the amino acid sequence of a naturally occurring parent peptide. Such an analog preferably has at least about 40%, at least about 45%, at least about 50%, at least about 55%, at least about 60%, at least about 65%, at least about 70%, at least about 75%, at least about 80%, at least about 85%, at least about 90%, or at least about 95% of the physiological activity of the parent peptide.

In some other embodiments, the analogs may be as physiologically active as the parent (i.e., has 100% of physiological activity of the parent peptide) or may be more than about 100%, more than about 110%, more than about 120%, more than about 130%, more than about 140%, more than about 150%, more than about 160%, more than about 170%, more than about 180%, more than about 190% or more than about 200% physiologically active than the parent peptide.

Such different amino acids may be additions, substitutions, deletions, or combinations thereof, including addition of non-natural side-chain groups and backbone links. Modifications of peptides to produce analogs thereof are known. See, e.g., U.S. Pat. No. 7,323,543; see also U.S. Pat. Nos. 7,482,171; 7,459,152; and 7,393,919, which are all incorporated herein by reference. For examples, analogs of peptides comprising HBD1 or analogs of fragments of HBD1 refer to either: i) structural analogs; ii) functional analogs; or iii) structural and functional analogs of HBD1 which are, inter alia, capable of replacing HBD1 in improving bone disorders, such as for example in preventing and/or treating bone disorders.

Analogs of the peptides of the present disclosure that have at least about 50%, at least about 55%, at least about 60%, at least about 65%, at least about 70%, at least about 75%, at least about 80%, at least about 85%, at least about 90%, at least about 95%, at least about 96%, at least about 97%, at least about 98% or at least 99% sequence homology with the amino acid sequences described herein over its full length, and sharing at least one of the metabolic effects or biological activity of HBD1. A person skilled in the art would readily identify an analog sequence of HBD1 or an analog sequence of a fragment of HBD1.

Analogs of HBD1 or analogs of fragment of HBD1 are, for example, analogs obtained by alanine scans or by amino acid substitutions. In some instances, analogs of HBD1 or analogs of fragments thereof may comprise a non-naturally encoded amino acid, wherein the non-naturally encoding amino acid refers to an amino acid that is not one of the common amino acids or pyrrolysine or selenocysteine, or an amino acid that occur by modification (e.g. post-translational modification) of naturally encoded amino acid (including, but not limited to, the 20 common amino acids or pyrrolysine and selenocysteine) but are not themselves incorporated into a growing polypeptide chain by the translation complex. Examples of such non-naturally-occurring amino acids include, but are not limited to, N-acetylglucosaminyl-L-serine, N-acetylglucosaminyl-L-threonine and O-phosphotyrosine.

Table 2 presents examples of analogs of HBD1 (3-11) with alanine substitutions at different amino acid positions.

TABLE 2

HBD1 (3-11) fragment with Alanine substitutions at various positions

| SEQ ID NOs | Amino Acid Sequence |
| --- | --- |
| SEQ ID NO: 17 | ALGLEEPKK |
| SEQ ID NO: 18 | HAGLEEPKK |

TABLE 2-continued

HBD1 (3-11) fragment with Alanine substitutions at various positions

| SEQ ID NOs | Amino Acid Sequence |
| --- | --- |
| SEQ ID NO: 19 | HLALEEPKK |
| SEQ ID NO: 20 | HLGAEEPKK |
| SEQ ID NO: 21 | HLGLAEPKK |
| SEQ ID NO: 22 | HLGLEAPKK |
| SEQ ID NO: 23 | HLGLEEAKK |
| SEQ ID NO: 24 | HLGLEEPAK |
| SEQ ID NO: 25 | HLGLEEPKA |

Table 3 presents other examples of analogs of HBD1 fragments comprising amino acid substitutions at different amino acid positions of HBD1 (3-11).

TABLE 3

Analogs of HBD1 (3-11) fragment with amino acid substitutions at various positions

| SEQ ID NOs | Amino Acid Sequence |
| --- | --- |
| SEQ ID NO: 26 | HLGLERPKK |
| SEQ ID NO: 27 | HLGLEFPKK |
| SEQ ID NO: 28 | HLGLEIPKK |
| SEQ ID NO: 29 | HLGLEPPKK |
| SEQ ID NO: 30 | HLGLESPKK |
| SEQ ID NO: 31 | HLGLEERKK |
| SEQ ID NO: 32 | HLGLEEFKK |
| SEQ ID NO: 33 | HLGLEELKK |
| SEQ ID NO: 34 | HLGLEESKK |
| SEQ ID NO: 35 | HLGLEEDKK |
| SEQ ID NO: 36 | HLGLEEPFK |
| SEQ ID NO: 37 | HLGLEEPPK |
| SEQ ID NO: 38 | HLGLEEPSK |
| SEQ ID NO: 39 | HLGLEEPDK |
| SEQ ID NO: 40 | HLGLEEPKF |
| SEQ ID NO: 41 | HLGLEEPKI |
| SEQ ID NO: 42 | HLGLEEPKP |
| SEQ ID NO: 43 | HLGLEEPKS |
| SEQ ID NO: 44 | HLGLEEPKD |
| SEQ ID NO: 45 | HLGLEEPIK |
| SEQ ID NO: 46 | HLGLEEPVK |
| SEQ ID NO: 47 | HLGLEEPQK |
| SEQ ID NO: 48 | HLGLEEPTK |

TABLE 3-continued

Analogs of HBD1 (3-11) fragment with amino acid substitutions at various positions

| SEQ ID NOs | Amino Acid Sequence |
|---|---|
| SEQ ID NO: 49 | HLGLEEPEK |
| SEQ ID NO: 50 | HLGLEEPKH |
| SEQ ID NO: 51 | HLGLEEPKR |
| SEQ ID NO: 52 | HLGLEEPKL |
| SEQ ID NO: 53 | HLGLEEPKM |
| SEQ ID NO: 54 | HLGLEEPKW |
| SEQ ID NO: 55 | HLGLEEPKV |
| SEQ ID NO: 56 | HLGLEEPKQ |
| SEQ ID NO: 57 | HLGLEEPKN |
| SEQ ID NO: 58 | HLGLEEPKY |
| SEQ ID NO: 59 | HLGLEEPKT |
| SEQ ID NO: 60 | HLGLEEPKE |
| SEQ ID NO: 61 | HLGLEEPSP |
| SEQ ID NO: 62 | HLGLEEPSS |
| SEQ ID NO: 89 | KLGLEEPKK |
| SEQ ID NO: 90 | HVGLEEPKK |
| SEQ ID NO: 91 | HLPLEEPKK |
| SEQ ID NO: 92 | HLGIEEPKK |
| SEQ ID NO: 93 | NLGLEEPKK |
| SEQ ID NO: 94 | HTGLEEPKK |
| SEQ ID NO: 95 | HLKLEEPKK |
| SEQ ID NO: 96 | HLGSEEPKK |
| SEQ ID NO: 97 | HLGLEEPYK |
| SEQ ID NO: 98 | HLGLEEPQK |
| SEQ ID NO: 99 | HLGLEEPNK |
| SEQ ID NO: 100 | HLGLEEPSF |
| SEQ ID NO: 101 | HLGLEEPSV |
| SEQ ID NO: 102 | HLGLEEPLM |
| SEQ ID NO: 103 | HLGLEEPLY |
| SEQ ID NO: 104 | HLGLEEPLN |
| SEQ ID NO: 105 | HLGLEEPLQ |
| SEQ ID NO: 106 | HLGLEEPFV |
| SEQ ID NO: 107 | HLGLEEPFQ |
| SEQ ID NO: 108 | HLGLEEPFN |
| SEQ ID NO: 109 | HLGLEEPVM |
| SEQ ID NO: 110 | HLGLEEPVN |
| SEQ ID NO: 111 | HLGLEEPMK |

In some instances, the analogs of HBD1 or fragments thereof may differ in sequence from HBD1 by 1, 2, 3, 4, 5, 6, 7, 8 or 9 amino acid substitutions, deletions, or additions, or combinations thereof.

In some instances, the amino acid substitution is a conservative amino acid substitution. As used herein the expression "conservative amino acid substitution" refers to substitutions that substitute a residue with another of like characteristics. Typical conservative amino acid substitutions include those among Gly (G), Ala (A), Val (V), Leu (L) and Ile (I); those among Ser (S), Cys (C), Met (M) and Thr (T); those among the acidic residues Asp (D) and Glu (E); those among Asn (N) and Gln (Q); those among the basic residues His (H), Lys (K) and Arg (R); and those among the aromatic residues Phe (F), Try (W) and Tyr (Y).

In some embodiments, the present technology provides an isolated peptide having a fragment of HBD1 as set forth in SEQ ID NO: 1. In some instances, the fragment is between 6 to 10 amino acids in length and comprises residues 3 to 10 of HBD1, namely: HLGLEEPK as set forth in SEQ ID NO: 7 or an analog thereof. Examples of analogs of a peptide having the amino acid sequence HLGLEEPK include, but are not limited to the peptides presented in Table 4.

TABLE 4

Analogs of HBD 1 (3-10) fragment with amino acid substitutions at various positions

| SEQ ID NO: | Amino Acid Sequence |
|---|---|
| SEQ ID NO: 112 | HLGLEEPR |
| SEQ ID NO: 113 | HLGLEEPH |

In some embodiments, the present technology provides an isolated peptide having a fragment of HBD1 as set forth in SEQ ID NO: 1. In some instances, the fragment is between 6 to 10 amino acids in length and comprises residues 5 to 10 of HBD1, namely: GLEEPK as set forth in SEQ ID NO: 14 or an analog thereof. In some other embodiments, the fragment is between 6 to 9 amino acids in length and comprises residues 5 to 10 of HBD1, namely: GLEEPK as set forth in SEQ ID NO: 14 or an analog thereof. Examples of analogs of a peptide having the amino acid sequence GLEEPK include, but are not limited to the peptides presented in Table 5.

TABLE 5

Analogs of HBD1 (5-10) fragment with amino acid substitutions at various positions

| SEQ ID NO: | Amino Acid Sequence |
|---|---|
| SEQ ID NO: 79 | GLEEPL |
| SEQ ID NO: 80 | GLEEPR |
| SEQ ID NO: 81 | GLDEPK |
| SEQ ID NO: 82 | GLEDPK |
| SEQ ID NO: 83 | GGEEPK |
| SEQ ID NO: 84 | GVEEPK |
| SEQ ID NO: 85 | GIEEPK |

TABLE 5-continued

Analogs of HBD1 (5-10) fragment with amino acid substitutions at various positions

| SEQ ID NO: | Amino Acid Sequence |
|---|---|
| SEQ ID NO: 86 | VLEEPK |
| SEQ ID NO: 87 | LLEEPK |
| SEQ ID NO: 88 | ILEEPK |

In some other embodiments, the peptides of the present disclosure may be modified. As used herein the term "modified" when used to qualify a peptide, refers to any changes made to a peptide, such as changes to the length of the peptide, the amino acid sequence, chemical structure, co-translational modification, or post-translational modification of a peptide. In some instances, the peptides of the present disclosure comprise one or more amino acid residues that are modified.

As used herein, the expression "post-translational modification" refers to any modification of a natural or non-natural amino acid that occurs to such an amino acid after it has been incorporated into a peptide chain. The term encompasses, by way of example only, co-translational in vivo modifications, co-translational in vitro modifications (such as in cell-free translation system), post-translational in vivo modifications, and post-translational in vitro modifications. Examples of post-translational modifications are, but are not limited to, glycosylation, pegylation, acetylation, acylation, amidation, methylation, carboxylation, phosphorylation, addition of salts, amides or esters, in particular C-terminal esters, and N-acyl derivatives of the peptides of the present disclosure. The types of post-translational modifications are well known in the art.

In some embodiments, the peptides of the present disclosure include one or more poly(ethylene glycol) (or "PEG") moiety of between about 10,000 and about 40,000 molecular weight coupled to either the N- or C-terminus of the peptide. "Polyalkylene glycol" means straight or branched polyalkylene glycol polymers including, but not limited to, polyethylene glycol (PEG), polypropylene glycol (PPG), and polybutylene glycol (PBG), as well as co-polymers of PEG, PPG and PBG in any combination, and includes the mono-alkylether of the polyalkylene glycol. Thus, in various embodiments of the present technology, the polyalkylene glycol in the peptides of the present disclosure can be, but is not limited to, polyethylene glycol, polypropylene glycol, polybutylene glycol, and any combination thereof. In certain embodiments, the polyalkylene glycol is polyethylene glycol or "PEG." The term "PEG subunit" refers to a single polyethylene glycol unit, i.e., —($CH_2CH_2O$)—.

In some embodiments, the polyalkylene glycol (e.g., PEG) can be non-polydispersed, monodispersed, substantially monodispersed, purely monodispersed, or substantially purely monodispersed. "Monodispersed" is used to describe a mixture of compounds wherein about 100 percent of the compounds in the mixture have the same molecular weight. "Substantially monodispersed" is used to describe a mixture of compounds wherein at least about 95 percent of the compounds in the mixture have the same molecular weight. "Purely monodispersed" is used to describe a mixture of compounds wherein about 100 percent of the compounds in the mixture have the same molecular weight and have the same molecular structure. Thus, a purely monodispersed mixture is a monodispersed mixture, but a monodispersed mixture is not necessarily a purely monodispersed mixture. "Substantially purely monodispersed" is used to describe a mixture of compounds wherein at least about 95 percent of the compounds in the mixture have the same molecular weight and have the same molecular structure. Thus, a substantially purely monodispersed mixture is a substantially monodispersed mixture, but a substantially monodispersed mixture is not necessarily a substantially purely monodispersed mixture. Table 6 presents examples of peptides of the present disclosure that are modified by pegylation.

TABLE 6

PEGylated HBD1 fragments

| SEQ ID NOs | Amino Acid Sequence |
|---|---|
| SEQ ID NO: 63 | PEG20-C-KHHLGLEEPKKLR |
| SEQ ID NO: 64 | KHHLGLEEPKKLR-C-PEG20 |
| SEQ ID NO: 65 | PEG20-C-HHLGLEEPKK |
| SEQ ID NO: 66 | HHLGLEEPKK-C-PEG20 |
| SEQ ID NO: 67 | PEG20-C-HLGLEEPKK |

In some other instances, the peptides of the present disclosure include one or more acyl group(s) coupled to any amino acid of the peptide. In some instances, the one or more acyl group(s) is coupled to the N-terminal or the C-terminal amino acid or to both. In some instances, acylation of the peptides of the present disclosure is a fatty acylation by which a fatty acid is added to one or more particular amino acid(s) of the peptide. Examples of fatty acylation include addition of: lauric acid (C12:0), tridecyclic acid (C13:0), myristic acid (C14:0), pentadecyclic acid (C15:0), palmitic acid (C16:0), margaric acid (C17:0), stearic acid (C18:0), nonadecyclic acid (C19:0), arachidinic acid (C20:0), heneicosylic acid (C21:0), behenic acid (C22:0), tricosylic acid (C23:0), or lignoceric acid (C24:0), or a mixture thereof to one or more amino acid of the peptides of the present disclosure.

In some variants, the fatty acid to be added may be unsaturated (e.g., monounsaturated or polyunsaturated). Examples of unsaturated fatty acids include but are not limited to: i) monounsaturated fatty acid: crotonic acid, myristoleic, palmitoleic acid, sapienic acid, oleic acid, elaidic acid, vaccenic acid, gadoleic, eicosenoic acid, erucic acid, nervonic acid; ii) di-unsaturated fatty acid: linoleic acid, eicosadienoic acid, docosadienoic acid; iii) tri-unsaturated fatty acids: linolenic acid, pinolenic acid, eleostearic acid, mead acid, dihomo-γ-linolenic acid, eicosatrienoic acid; iv) tetra-unsaturated fatty acid: stearidonic acid, arachidonic acid, eicosatetraenoic acid, adrenic acid; v) pentaunsaturated fatty acids: bosseopentaenoic acid, eicosapentaenoic acid, ozubondo acid, sardine acid, tetracosanolpentaenoic acid; and vi) hexa-unsaturated fatty acids: docosahexaenoic acid, and herring acid.

In some embodiments, the peptides of the present disclosure may be coupled to fatty acids that comprise one or more carboxylic functional groups (—COOH).

The methods for carrying acylation of peptides are well known in the art. Table 7 presents examples of peptides of the present disclosure that are modified by acylation.

TABLE 7

Acylated HBD1 (2-11) fragments

| SEQ ID NOs | Amino Acid Sequence |
|---|---|
| SEQ ID NO: 68 | C16:0-HHLGLEEPKK |
| SEQ ID NO: 69 | C18:0-HHLGLEEPKK |
| SEQ ID NO: 70 | C20:0-HHLGLEEPKK |
| SEQ ID NO: 71 | C14:0-HLGLEEPKK |
| SEQ ID NO: 72 | C16:0-HLGLEEPKK |
| SEQ ID NO: 73 | C18:0-HLGLEEPKK |
| SEQ ID NO: 74 | C20:0-HLGLEEPKK |
| SEQ ID NO: 75 | C16:0-diacid-HLGLEEPKK |
| SEQ ID NO: 76 | HLGLEEPKK-C16:0 |
| SEQ ID NO: 78 | C16:0-KHHLGLEEPKKLR |

In some additional embodiments, the peptides of the present disclosure may be coupled to a linker or a linker group (e.g., linker moiety). As used herein, the expression "linker" or "linking group" includes non-amino acid linking groups such as are known in the art (see, e.g., U.S. Pat. Nos. 7,468,418; 7,402,652; and 7,351,797, which are all incorporated herein by reference) or variations thereof that will be apparent to those skilled in the art.

In some embodiments, the peptides of the present disclosure may include more than one modification (e.g., may include a PEG group and an acyl group).

In some other embodiments, the peptides of the present disclosure may be coupled to a modifying group which is itself modified. For example, the peptides of the present disclosure may be coupled to a fatty acid which is itself modified. The modified fatty acid may, for example, be coupled to a linker or a linker group and the linker or the linker group may itself be coupled to another modifying group such as a PEG group or one or more carboxylic functional groups (—COOH). Various combinations of modifications and the methods for achieving them will be recognized and appreciated by those skilled in the art.

Certain aspects of the present technology use polynucleotides. These polynucleotides include isolated polynucleotides which encode the HBD1 peptides, fragments and analogs defined herein.

As used herein, the term "polynucleotide" refers to a molecule comprised of a plurality of deoxyribonucleotides or nucleoside subunits. The linkage between the nucleoside subunits can be provided by phosphates, phosphonates, phosphoramidates, phosphorothioates, or the like, or by nonphosphate groups as are known in the art, such as peptoid-type linkages utilized in peptide nucleic acids (PNAs). The linking groups can be chiral or achiral. The oligonucleotides or polynucleotides can range in length from 2 nucleoside subunits to hundreds or thousands of nucleoside subunits. While oligonucleotides are preferably 5 to 100 subunits in length, and more preferably, 5 to 60 subunits in length, the length of polynucleotides can be much greater (e.g., up to 100). The polynucleotide may be any of DNA and RNA. The DNA may be in any form of genomic DNA, a genomic DNA library, cDNA derived from a cell or tissue, and synthetic DNA. Moreover, the present disclosure may, in certain aspects, use vectors which include bacteriophage, plasmid, cosmid, or phagemid.

The polypeptides useful in the present technology may be prepared in any suitable manner as known in the art. Such polypeptides include isolated naturally occurring polypeptides, recombinantly produced polypeptides, synthetically produced polypeptides, or polypeptides produced by a combination of these methods. Means and methods for preparing such polypeptides are well known in the art.

B. Therapeutic Actions

As used herein, the terms "treat," "treating" and "treatment" as used herein all refer to any type of treatment that imparts a benefit to a subject afflicted with a disease, including improvement in the condition of the patient (e.g., in one or more symptoms), delay in the progression of the disease, or the like.

As used herein, the terms "subjects" and "patient" generally relate to human subjects and are used interchangeably. The subjects may be male or female and may be of any race or ethnicity, including, but not limited to, Caucasian, African-American, African, Asian, Hispanic, Indian, etc. The subjects may be of any age, including newborn, neonate, infant, child, adolescent, adult, and geriatric. In some embodiments the subjects are afflicted with a bone disorder. Subjects may also include animal subjects, particularly mammalian subjects such as canines, felines, bovines, caprines, equines, ovines, porcines, rodents (e.g. rats and mice), lagomorphs, primates (including non-human primates), etc., for veterinary medicine or pharmaceutical drug development purposes.

In some embodiments, the peptides of the present disclosure may be used for improving and/or ameliorating a bone disorder (or used in a method for improving and/or ameliorating a bone disorder). In some instances, the peptides of the present disclosure may be used to prevent a bone disorder, in some other instance the peptides of the present disclosure may be used to treat a bone disorder, in some other instances, the peptides of the present disclosure may be used to both prevent and treat a bone disorder.

As used herein, the expression "bone disorder" refers to any of several diseases that cause various abnormalities or deformities of one or more bones and/or to bone cells. Examples of bone disorders include: osteoporosis, rickets, osteomalacia, osteogenesis imperfecta, marble bone disease (osteopetrosis), fibrous dysplasia, postmenopausal osteoporosis, senile osteoporosis in males and females, glucocorticoid-induced osteoporosis, immobilization-induced osteoporosis, weightlessness-induced osteoporosis, post-transplantation osteoporosis, migratory osteoporosis, idiopathic osteoporosis, juvenile osteoporosis, Paget's Disease, chronic hyperparathyroidism, hyperthyroidism, rheumatoid arthritis, Gorham-Stout disease, McCune-Albright syndrome, osteolytic metastases of various cancers or multiple myeloma.

As used herein, the expression "bone disorders" also include loss of bone mass, general bone fragility, joint degeneration, non-union fractures, orthopedic and dental problems caused by diabetes, periimplantitis, poor responses to bone grafts/implants/bone substitute materials, periodontal diseases, skeletal aging, broken bones, bone defects, bone transplant, bone grafts, bone cancer, joint replacements, joint repair, fusion, facet repair, bone degeneration, dental implants and repair, bone marrow deficits and other conditions associated with bone and boney tissue. Bone defects may be a gap, deformation and/or a nonunion fracture in a bone. Bone disorders also include osteopathy in acromegalic patients, cystic fibrosis-related bone disease, adynamic bone disease, renal osteodystrophy associated with chronic kidney disease, bone disease associated with cystinosis and bone disease associated with hyperoxaluria.

Bone degeneration may be due to osteopenia or osteoporosis (e.g. the patient is afflicted with geriatric or senile osteoporosis, with post-menopausal osteoporosis, etc.), or due to dwarfism.

Joint replacements that may be treated include vertebral, knee, hip, tarsal, phalangeal, elbow, ankle and/or other articulating joints or replacements thereof. Joint repairs include, but are not limited to, vertebral, knee, hip, tarsal, phalangeal, elbow, ankle, and sacroiliac joint repairs.

In some embodiments, the peptides of the present disclosure may be used to enhance bone formation (i.e., increasing the amount of new bone that is laid down, or used in a method to enhance bone formation).

In some other embodiments, the peptides of the present disclosure may be used to inhibit bone resorption (i.e., to reduce the amount of bone that is dissolved) (or used in a method to inhibit bone resorption) simultaneously in a subject in need thereof. Non-limiting examples of subjects for whom such treatment would be indicated and/or beneficial include women (e.g., postmenopausal; premenopausal) with osteoporosis or low bone mass, men with osteoporosis or low bone mass, subjects with a healing fracture, subjects undergoing prolonged immobilization, subjects who have been or are immobilized for a prolonged period, subjects likely to undergo or experience prolonged immobilization, subjects with estrogen deficiency, etc., as would be known in the art.

In some further embodiments, the peptides of the present disclosure may be used for inducing deposition and maturation of bone in a subject in need thereof (e.g., a subject having a bone disorder) (or used in a method for inducing deposition and maturation of bone). In some instances, the peptide of the present disclosure may be used in combination with a bone resorption inhibitor.

In some aspects of these embodiments, the bone disorder is at a targeted site of the subject. The targeted site may be an intervertebral space, a facet joint, a site of a bone fracture, bones of the mouth, chin and jaw, or an implant site.

HBD1 was shown to modulate bone mass acquisition and osteoblast differentiation (Kawai, J B C, 2011; Xi, JBMR, 2014). In view of this, it is reasonable to infer that fragments of HBD1 that retain the physiological activities of HBD1 could also modulate bone mass acquisition and osteoblast differentiation. As such, in some embodiments, the peptides of the present disclosure may be used to inhibit fat cell differentiation (e.g., inhibiting fat cell precursor differentiation into mature adipocytes) in the subject. In some other embodiments, the peptides of the present disclosure may be used to modulate fat mass in a subject.

In some embodiments, the peptides of the present disclosure may be employed in methods of in vitro or ex vivo expansion of stem cells, carried out according to protocols known in the art. Thus, the present disclosure provides a method of expanding stem cells in vitro or ex vivo, comprising contacting the peptides of the present disclosure with stem cells from a subject, wherein said stem cells are maintained under conditions whereby they are reintroduced into the subject. For example in some ex vivo embodiments, the stem cells are obtained from a subject, e.g., a human, e.g., from peripheral blood, umbilical cord blood, or bone marrow, and the stem cells are contacted with the compound of this present disclosure outside the body of the subject. Ex vivo embodiments include obtaining stem cells from a subject and culturing the cells for a period of time prior to use (e.g., for transplantation). In some embodiments, after contact with the peptides of the present disclosure, the cells are delivered to a subject, e.g., the same subject from which the cells were isolated (autologous donation) or a different subject (non-autologous (e.g., syngeneic or allogeneic) donation). Non-limiting examples of a subject for whom these methods would be indicated or beneficial include a subject having or who has had chemotherapy, a subject having or who has had radiation, a subject having aplastic anemia, a subject having myelodysplasia, and any combination thereof.

In some embodiments, the uses and methods defined herein comprise administering to a subject a therapeutically effective amount of a peptide as defined herein to achieve the effects discussed here (e.g., to prevent and/or treat a bone disorder).

Therapeutically effective dosage of any specific peptide of the present disclosure will vary from peptide to peptide, patient to patient, and subject to subject, and will depend, among other things, upon the effect or result to be achieved, the condition of the patient and the route of delivery. In some embodiments, a dosage is from about 1 µg/kg to about 1 mg/kg. In some other embodiments, a dosage is from about 1 mg/kg to about 50 mg/kg.

In some instances, the dosage is from about 0.001 mg/kg, about 0.05 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg or about 1.0 mg/kg, up to about 30 mg/kg, or about 40 mg/kg.

In some other instances, the dosage is about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, about 20 mg/kg, about 21 mg/kg, about 22 mg/kg, about 23 mg/kg, about 24 mg/kg, about 25 mg/kg, about 26 mg/kg, about 27 mg/kg, about 28 mg/kg, about 29 mg/kg, about 30 mg/kg, about 31 mg/kg, about 32 mg/kg, about 33 mg/kg, about 34 mg/kg, about 35 mg/kg, about 36 mg/kg, about 37 mg/kg, about 38 mg/kg, about 39 mg/kg, about 40 mg/kg, about 41 mg/kg, about 42 mg/kg, about 43 mg/kg, about 44 mg/kg, about 45 mg/kg, about 46 mg/kg, about 47 mg/kg, about 48 mg/kg, about 49 mg/kg, or about 50 mg/kg or more may be used.

Additional examples of therapeutically effective dosages include: between about 1 and about 50 mg/kg/96 hr; between about 1 and about 50 mg/kg/48 hr; between about 1 and about 50 mg/kg/36 hr; between about 1 and about 50 mg/kg/24 hr; between about 1 and about 50 mg/kg/12 hr; between about 1 and about 25 mg/kg/96 hr; between about 1 and about 25 mg/kg/48 hr; between about 1 and about 25 mg/kg/36 hr; between about 1 and about 25 mg/kg/24 hr; between about 1 and about 25 mg/kg/12 hr; between about 1 and about 10 mg/kg/96 hr; between about 1 and about 10 mg/kg/48 hr; between about 1 and about 10 mg/kg/36 hr; between about 1 and about 10 mg/kg/24 hr; between about 1 and about 10 mg/kg/12 hr; between about 1 and about 5 mg/kg/96 hr; between about 1 and about 5 mg/kg/48 hr; between about 1 and about 5 mg/kg/36 hr; between about 1 and about 5 mg/kg/24 hr; between about 1 and about 5 mg/kg/12 hr; between about 0.001 and about 1 mg/kg/96 hr; between about 0.001 and about 1 mg/kg/48 hr; between about 0.001 and about 1 mg/kg/36 hr; between about 0.001 and about 1 mg/kg/24 hr; and between about 0.001 and about 1 mg/kg/12 hr.

"Concurrently administering" or "concurrently administer" as used herein means that the two or more peptides, compounds or compositions are administered closely enough in time to produce a combined effect (that is, concurrently may be simultaneously, or it may be two or more events occurring within a short time period before or after each other, e.g., sequentially). Simultaneous concurrent administration may be carried out by, for example, mixing the compounds prior to administration, or by administering the compounds at the same point in time but at different anatomic sites and/or by using different routes of administration.

C. Pharmaceutical Compositions

As used herein, the expression "active agent" refers to a peptide as defined herein.

The expressions "therapeutically acceptable", "therapeutically suitable", "pharmaceutically acceptable" and "pharmaceutically suitable" are used interchangeably herein and refer to a peptide, a compound, or a composition that is suitable for administration to a subject to achieve the effects described herein, such as the treatment defined herein, without unduly deleterious side effects in light of the severity of the disease and necessity of the treatment.

The peptides described above may be formulated for administration in a pharmaceutical carrier in accordance with known techniques. See, e.g., Remington, The Science And Practice of Pharmacy (9th Ed. 1995). In the manufacture of a pharmaceutical composition according to the present disclosure, the peptide (including the physiologically acceptable salts thereof) is typically admixed with, inter alia, an acceptable carrier. The carrier must, of course, be acceptable in the sense of being compatible with any other ingredients in the composition and must not be deleterious to the patient. The carrier may be a solid or a liquid, or both, and is preferably formulated with the peptide as a unit-dose formulation, for example, a tablet, which may contain from about 0.01 or about 0.5% to about 95% or about 99% by weight of the peptide. One or more active compounds may be incorporated in the compositions of the present disclosure, which may be prepared by any of the well-known techniques of pharmacy comprising admixing the components, optionally including one or more accessory ingredients.

The composition of the present disclosure include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular peptide which is being used.

Compositions suitable for oral administration may be presented in discrete units, such as capsules, cachets, lozenges, or tablets, each containing a predetermined amount of the peptide; as a powder or granules; as a solution or a suspension in an aqueous or non-aqueous liquid; or as an oil-in-water or water-in-oil emulsion. Such compositions may be prepared by any suitable method of pharmacy which includes the step of bringing into association the peptide and a suitable carrier (which may contain one or more accessory ingredients as noted above). In general, the compositions of the present disclosure are prepared by uniformly and intimately admixing the peptide with a liquid or finely divided solid carrier, or both, and then, if necessary, shaping the resulting mixture. For example, a tablet may be prepared by compressing or molding a powder or granules containing the peptide, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Compositions suitable for buccal (sub-lingual) administration include lozenges comprising the peptide in a flavoured base, usually sucrose and acacia or tragacanth; and pastilles comprising the peptide in an inert base such as gelatin and glycerin or sucrose and acacia.

Compositions of the present disclosure suitable for parenteral administration comprise sterile aqueous and non-aqueous injection solutions of the peptide, which preparations are preferably isotonic with the blood of the intended recipient. These preparations may contain anti-oxidants, buffers, bacteriostats and solutes which render the composition isotonic with the blood of the intended recipient. Aqueous and non-aqueous sterile suspensions may include suspending agents and thickening agents. The composition may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present disclosure, there is provided an injectable, stable, sterile composition comprising a peptide as defined herein, or a salt thereof, in a unit dosage form in a sealed container. The peptide or salt is provided in the form of a lyophilizate which is capable of being reconstituted with a suitable pharmaceutically acceptable carrier to form a liquid composition suitable for injection thereof into a subject. The unit dosage form typically comprises from about 10 mg to about 10 grams of the peptide or salt. When the peptide or salt is substantially water-insoluble, a sufficient amount of emulsifying agent which is physiologically acceptable may be employed in sufficient quantity to emulsify the compound or salt in an aqueous carrier. One such useful emulsifying agent is phosphatidyl choline.

Compositions suitable for rectal administration are preferably presented as unit dose suppositories. These may be prepared by admixing the peptide as defined herein with one or more conventional solid carriers, for example, cocoa butter, and then shaping the resulting mixture.

Compositions suitable for topical application to the skin preferably take the form of an ointment, cream, lotion, paste, gel, spray, aerosol, or oil. Carriers which may be used include petroleum jelly, lanoline, polyethylene glycols, alcohols, transdermal enhancers, and combinations of two or more thereof.

Compositions suitable for transdermal administration may be presented as discrete patches adapted to remain in intimate contact with the epidermis of the recipient for a prolonged period of time. Compositions suitable for transdermal administration may also be delivered by iontophoresis (see, for example, Pharmaceutical Research 3 (6):318 (1986)) and typically take the form of an optionally buffered aqueous solution of the peptide as defined herein. Suitable compositions comprise citrate or bis\tris buffer (pH 6) or ethanol/water and contain from 0.1M to 0.2M active ingredient.

Further, the present disclosure provides liposomal formulations of the peptide disclosed herein and salts thereof. The technology for forming liposomal suspensions is well known in the art. When the peptide as defined herein or salt thereof is an aqueous-soluble salt, using conventional liposome technology, the same may be incorporated into lipid vesicles. In such an instance, due to the water solubility of the peptide or salt, the peptide or salt will be substantially entrained within the hydrophilic center or core of the liposomes. The lipid layer employed may be of any conventional composition and may either contain cholesterol or may be cholesterol-free. When the peptide or salt of interest is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

The liposomal formulations containing the active agents disclosed herein or salts thereof, may be lyophilized to produce a lyophilizate which may be reconstituted with a pharmaceutically acceptable carrier, such as water, to regenerate a liposomal suspension.

Other pharmaceutical compositions may be prepared from the water-insoluble active agent disclosed herein, or salts thereof, such as aqueous base emulsions. In such an instance, the composition will contain a sufficient amount of pharmaceutically acceptable emulsifying agent to emulsify the desired amount of the active agent or salt thereof. Particularly useful emulsifying agents include phosphatidyl cholines, and lecithin.

In some embodiments, the peptides of the present disclosure may be delivered to a subject in need thereof using a medical device, in particular using orthopedic medical devices. Examples of medical devices that may be useful for delivering the peptides of the present disclosure include, but are not limited to, sponges (e.g., collagen sponges, gelatin sponges, or the like), dressing, gauges, stents, cages (e.g., intervertebral cages, fusion cages, or the like), bone cement, bone mixers, bone substitutes, pins, anchors, buttons, prostheses, screws (e.g., facet screws, pedicle screw systems, bone screws, or the like), spacers, intramedullary nails, stems (e.g., hip stems or the like), custom implants, plates (e.g., humerous plates, wrist plates, radius plates, cervical plates, lumbar plates or the like), and trauma products. In these embodiments, the peptides of the present disclosure may be incorporated into the materials used to make the medical device or may be applied onto the materials used to make the medical devices or onto the medical device itself.

In some other embodiments, the peptides of the present disclosure may be delivered to a subject in need thereof using a delivery device such as a particle (e.g., nanoparticles or microparticles) or an encapsulation system (e.g., microcapsules, microspheres). In some instances, the peptides of the present disclosure may be dispersed throughout the materials forming the delivery systems, such as for example, polymeric chains, or may be located into pores or cavities formed into the delivery system. In some instances, the release of the peptides from such delivery systems may be controlled (i.e., slow release, sustained release or controlled release). Examples of particles and particles and encapsulation systems that may be used to deliver the peptides of the present disclosure are well known in the art.

In addition to active compound(s), the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use.

In some embodiments, the present technology provides for kits comprising one or more peptides as defined herein together with instructions for use of kit according to the applications defined herein.

Identification of equivalent peptides, compounds, compositions, methods, uses and kits are well within the skill of the ordinary practitioner and would require no more than routine experimentation, in light of the teachings of the present disclosure. Practice of the disclosure will be still more fully understood from the following examples, which are presented herein for illustration only and should not be construed as limiting the disclosure in any way.

EXAMPLES

The examples below are given so as to illustrate the practice of various embodiments of the present technology. They are not intended to limit or define the entire scope of this technology. It should be appreciated that the technology is not limited to the particular embodiments described and illustrated herein but includes all modifications and variations falling within the scope of the disclosure as defined in the appended embodiments.

Example 1: Effect of HBD1 Fragments on Osteocalcin Expression During In Vitro Osteoblast Differentiation Peptides were manufactured according to a standard manufacturing process in peptide chemistry by solid phase peptide synthesis (SPPS) using the Fmoc (9-fluorenylmethyloxycarbonyl) strategy (Merrifield, R. B. Solid phase peptide synthesis. I. The synthesis of a tetrapeptide. J. Am. Chem. Soc. 1963, 85, 2149-2154). Identity of the peptides was verified by LC-MS. The purity (at least 95%) and the net peptide content of peptides were determined by RP-HPLC and elemental analysis, respectively.

Each peptide was tested in a biologic assay measuring its ability to stimulate differentiation of osteoblast cells over a 18-21 day interval (Table 8) or a 14-15 day interval (Table 9) as assessed by the stimulation of osteocalcin protein synthesis. MC-3T3 E1 clone 4 (CL4) osteoblast cells were obtained from ATCC (Manassas, Va., USA). Cells were cultured in α-MEM containing 10% fetal bovine serum (FBS; Thermo Fisher Scientific, Pittsburgh, Pa., USA). After confluency, culture medium was changed to differentiation medium (DM), which contained 10% FBS plus 50 µg/mL ascorbic acid and 4 mM β-glycerol phosphate, with or without a test peptide (1 µg/mL in Table 8 or 1 µmol/L in Table 9). Fresh DM, with or without test peptide, was applied every 72 hours. The cell monolayers were lysed in a modified radioimmunoprecipitation assay (RIPA) buffer. Total cellular protein in the lysates was determined using BCA (Thermo Fisher Scientific, Rockford, Ill., USA). Cell proteins are separated on SDS-PAGE gel and transferred on PVDF membrane for analysis. Osteocalcin detection was performed using anti-osteocalcin antibody at 1:200 dilution (Santa Cruz Biotechnology, Inc, Santa Cruz, Calif., USA) or at 1:3000 dilution (NPT Inc., Chapel Hill, N.C., USA) and visualized using enhanced chemiluminescence (Thermo Fisher Scientific, Rockford, Ill., USA).

In this series of experiments, fragments of HBD1 of various lengths were tested for their potency in an in vitro osteoblast differentiation bioassay. The results presented in Tables 8 and 9 show that, surprisingly, some fragments as short as 6, 7, 8, 9 or 10 amino acids in length exhibit potency in this assay. The deletion of amino acids R, L and the first K at the C-terminus of the peptide such as: HBD1 (1-12), HBD1 (1-11), HBD1 (3-11), HBD1 (4-11) and HBD1 (4-10) resulted in biologically active peptides. Similarly, deletions of K, H and H at the N-terminus of the peptide such as: HBD1 (3-13) and HBD1 (4-13) also resulted in some preserved biological activity. By combining deletions at both the N- and C-terminus of the peptide, the shortest active fragment was HBD1 (5-10), a 6 amino acid-long peptide as set forth in SEQ ID NO: 14.

TABLE 8

Ability of the peptides to stimulate differentiation of osteoblast cells

| Fragment | Peptide Sequence | Potency | Fold increase vs DM ± SD |
|---|---|---|---|
| Control | DM | | 1 |
| HBD1 (1-13) | KHHLGLEEPKKLR (SEQ ID NO: 1) | + | 3.28 ± 0.72 |
| HBD1 (2-13) | _HHLGLEEPKKLR (SEQ ID NO: 2) | + | 3.45 ± 0.46 |
| HBD1 (3-13) | __HLGLEEPKKLR (SEQ ID NO: 3) | + | 3.04 ± 0.66 |
| HBD1 (4-13) | ___LGLEEPKKLR (SEQ ID NO: 4) | + | 3.91 ± 0.88 |
| HBD1 (1-12) | KHHLGLEEPKKL_ (SEQ ID NO: 5) | + | 4.05 ± 0.95 |
| HBD1 (1-11) | KHHLGLEEPKK__ (SEQ ID NO: 6) | + | 3.91 ± 0.60 |
| HBD1 (3-10) | __HLGLEEPK___ (SEQ ID NO: 7) | + | 4.09 ± 0.87 |
| HBD1 (3-9) | __HLGLEEP____ (SEQ ID NO: 8) | ± | 2.01 ± 0.30 |
| HBD1 (3-12) | __HLGLEEPKKL_ (SEQ ID NO: 9) | + | 4.25 ± 0.60 |

TABLE 9

Ability of the peptides to stimulate differentiation of osteoblast cells

| Fragment | Peptide Sequence | Potency | Fold increase vs DM ± SD |
|---|---|---|---|
| Control | DM | | 1 |
| HBD1 (3-11) | __HLGLEEPKK__ (SEQ ID NO: 10) | + | 2.51 ± 0.42 |
| HBD1 (4-11) | ___LGLEEPKK__ (SEQ ID NO: 11) | + | 2.93 ± 0.54 |
| HBD1 (5-11) | ____GLEEPKK__ (SEQ ID NO: 12) | + | 2.03 ± 0.68 |

TABLE 9-continued

Ability of the peptides to stimulate differentiation of osteoblast cells

| Fragment | Peptide Sequence | Potency | Fold increase vs DM ± SD |
|---|---|---|---|
| HBD1 (4-10) | ___LGLEEPK___ (SEQ ID NO: 13) | + | 1.83 ± 0.52 |
| HBD1 (5-10) | ____GLEEPK___ (SEQ ID NO: 14) | + | 1.83 ± 0.53 |
| HBD1 (4-9) | ___LGLEEP____ (SEQ ID NO: 15) | + | 1.29 ± 0.23 |
| HBD1 (2-11) | _HHLGLEEPKK__ (SEQ ID NO: 16) | + | 3.28 ± 0.36 |

Example 2: Effects of Various Doses of HBD1 Fragments on Osteocalcin Expression During In Vitro Osteoblast Differentiation The HBD1 (3-11) peptide as set forth in SEQ ID NO: 10 was manufactured according to a standard manufacturing process in peptide chemistry by solid phase peptide synthesis (SPPS) using the Fmoc (9-fluorenylmethyloxycarbonyl) strategy (Merrifield, R. B. Solid phase peptide synthesis. I. The synthesis of a tetrapeptide. J. Am. Chem. Soc. 1963, 85, 2149-2154). The identity of the peptide was verified by LC-MS. The purity (at least 95%) and the net peptide were determined by RP-HPLC and elemental analysis, respectively.

The peptide was tested at different concentrations in a biologic assay measuring its ability to stimulate differentiation of osteoblast cells over a 18 day interval as assessed by the stimulation of osteocalcin protein synthesis. MC-3T3 E1 clone 4 (CL4) osteoblast cells were obtained from ATCC (Manassas, Va., USA). Cells were cultured in α-MEM containing 10% fetal bovine serum (FBS; Thermo Fisher Scientific, Pittsburgh, Pa., USA). After confluency, culture medium was changed to differentiation medium (DM), which contained 10% FBS plus 50 μg/mL ascorbic acid and 4 mM β-glycerol phosphate, with or without an ascending dose of the peptide from 0.1 μg/mL to 4 μg/mL. Fresh DM, with or without the peptide, was applied every 72 hours. The cell monolayers were lysed in a modified radioimmunoprecipitation assay (RIPA) buffer. Total cellular protein in the lysates was determined using BCA (Thermo Fisher Scientific, Rockford, Ill., USA). Cell proteins are separated on SDS-PAGE gel and transferred on PVDF membrane for analysis. Osteocalcin detection was performed using anti-osteocalcin antibody at 1:200 dilution (Santa Cruz Biotechnology, Inc, Santa Cruz, Calif., USA) and visualized using enhanced chemiluminescence (Thermo Fisher Scientific, Rockford, Ill., USA).

In this experiment, HBD1 (3-11) was tested at several doses in the osteoblast differentiation assay. The results of this experiment are summarized in Table 10 below. The results show that this peptide improved osteoblast differentiation in a dose-dependent fashion, exhibiting high potency at the highest doses tested. This suggests a therapeutic potential for HBD1 (3-11) in bone disorders, as either an isolated peptide, an analog thereof, or as a sequence in a larger peptide, or conjugated to a chemical moiety, and administered alone or in combination with anabolic or anti-resorptive agents.

TABLE 10

Ability of various doses of the HBD1 (3-11) peptide to stimulate differentiation of osteoblast cells

| Fragment | Peptide Sequence | Dose | Potency | Fold increase vs DM ± SD |
|---|---|---|---|---|
| Control | DM | | | 1 |
| HBD1 (3-11) | HLGLEEPKK (SEQ ID NO: 10) | 0.1 | - | ± 0.15 |
| | | 0.25 | + | 1.81 ± 0.15 |
| | | 0.5 | + | 2.5 ± 0.39 |
| | | 1.0 | + | 3.28 ± 0.72 |
| | | 2.0 | + | 3.67 ± 0.83 |
| | | 3.0 | + | 3.91 ± 0.87 |
| | | 4.0 | + | 4.59 ± 1.19 |

Example 3: Effect of HBD1 Fragment Analogs with Alanine Substitutions on Osteocalcin Expression During In Vitro Osteoblast Differentiation The peptides were manufactured according to a standard manufacturing process in peptide chemistry by solid phase peptide synthesis (SPPS) using the Fmoc (9-fluorenylmethyloxycarbonyl) strategy (Merrifield, R. B. Solid phase peptide synthesis. I. The synthesis of a tetrapeptide. J. Am. Chem. Soc. 1963, 85, 2149-2154). Identity of peptides was verified by LC-MS. The purity (at least 95%) and the net peptide content of peptides were determined by RP-HPLC and elemental analysis, respectively.

Each peptide was tested in a biologic assay measuring its ability to stimulate differentiation of osteoblast cells over a 15 day interval as assessed by the stimulation of osteocalcin protein synthesis. MC-3T3 E1 clone 4 (CL4) osteoblast cells were obtained from ATCC (Manassas, Va., USA). Cells were cultured in α-MEM containing 10% fetal bovine serum (FBS; Thermo Fisher Scientific, Pittsburgh, Pa., USA). After confluency, culture medium was changed to differentiation medium (DM), which contained 10% FBS plus 50 µg/mL ascorbic acid and 4 mM β-glycerol phosphate, with or without a test peptide (1 µg/mL). Fresh DM, with or without test peptide, was applied every 72 hours for 15 days. The cell monolayers were lysed in a modified radioimmunoprecipitation assay (RIPA) buffer. Total cellular protein in the lysates was determined using BCA (Thermo Fisher Scientific, Rockford, Ill., USA). Cell proteins are separated on SDS-PAGE gel and transferred on PVDF membrane for analysis. Osteocalcin detection was performed using anti-osteocalcin antibody at 1:200 dilution (Santa Cruz Biotechnology, Inc, Santa Cruz, Calif., USA) and visualized using enhanced chemiluminescence (Thermo Fisher Scientific, Rockford, Ill., USA).

In these experiments, the effect of substituting each amino-acid of the parent HBD1 (3-11) peptide as set forth in SEQ ID NO: 10 was examined Each Ala-monosubstituted peptide were synthesized and tested on the in vitro osteoblast differentiation assay. Results shown in Table 11 indicate that alanine substitutions of HBD1 (3-11) at positions 3, 8, 9, 10 or 11 generated compounds with residual biological activity Alanine substitutions on positions 4, 5, 6 or 7 resulted in a decrease in biological activity, suggesting that the side chains of L(4) G (5), L(6) and E(7) are important for biological activity. Altogether, these data show that amino acid substitutions with natural or non-natural amino acids can be performed on this 9 amino acid long peptide and may generate analogs with preserved or increase biological activity.

TABLE 11

Ability of HBD1 fragments with Ala-monosubstitutions to stimulate differentiation of osteoblast cells

| SEQ ID NO: | Peptide Sequence | Potency | Fold increase vs SEQ ID NO: 10 ± SE |
|---|---|---|---|
| 10 | HLGLEEPKK | + | 1 |
| 17 | ALGLEEPKK | - | 0.64 ± 0.08 |
| 18 | HAGLEEPKK | - | 0.41 ± 0.05 |
| 19 | HLALEEPKK | - | 0.29 ± 0.04 |
| 20 | HLGAEEPKK | - | 0.38 ± 0.05 |
| 21 | HLGLAEPKK | - | 0.20 ± 0.03 |
| 22 | HLGLEAPKK | + | 1.00 ± 0.10 |
| 23 | HLGLEEAKK | + | 1.12 ± 0.11 |
| 24 | HLGLEEPAK | + | 1.25 ± 0.13 |
| 25 | HLGLEEPKA | + | 0.87 ± 0.09 |

Example 5: Effects of HBD1 Fragment Analogs with Amino-Acid Substitutions on Osteocalcin Expression During In Vitro Osteoblast Differentiation The peptides were manufactured according to a standard manufacturing process in peptide chemistry by solid phase peptide synthesis (SPPS) using the Fmoc (9-fluorenylmethyloxycarbonyl) strategy (Merrifield, R. B. Solid phase peptide synthesis. I. The synthesis of a tetrapeptide. J. Am. Chem. Soc. 1963, 85, 2149-2154). Identity of peptides was verified by LC-MS. The purity (at least 95%) and the net peptide content of peptides were determined by RP-HPLC and elemental analysis, respectively.

Each peptide was tested in a biologic assay measuring its ability to stimulate differentiation of osteoblast cells over a 12 day interval in Table 12, Table 15 and Table 16 or a 15 day interval in Table 13 and Table 14 as assessed by the stimulation of osteocalcin protein synthesis. MC-3T3 E1 clone 4 (CL4) osteoblast cells were obtained from ATCC (Manassas, Va., USA). Cells were cultured in α-MEM containing 10% fetal bovine serum (FBS; Thermo Fisher Scientific, Pittsburgh, Pa., USA). After confluency, culture medium was changed to differentiation medium (DM), which contained 10% FBS plus 50 µg/mL ascorbic acid and 4 mM β-glycerol phosphate, with or without a test peptide (1 µmon). Fresh DM, with or without test peptide, was applied every 72 hours. The cell monolayers were lysed in a modified radioimmunoprecipitation assay (RIPA) buffer. Total cellular protein in the lysates was determined using BCA (Thermo Fisher Scientific, Rockford, Ill., USA). Cell proteins are separated on SDS-PAGE gel and transferred on PVDF membrane for analysis. Osteocalcin detection was performed using anti-osteocalcin antibody at 1:3000 dilution (NPT Inc., Chapel Hill, N.C., USA) and visualized using enhanced chemiluminescence (Thermo Fisher Scientific, Rockford, Ill., USA).

In these experiments, the effect of amino-acid substitutions on positions 8, 9, 10 and 11 of the parent HBD1 (3-11) peptide was examined Each of the mono- or poly-substituted peptides were synthesized and tested on the in vitro osteoblast differentiation assay. Results shown in Tables 12, 13 and 14 indicate that conservative or non-conservative substitutions yielded peptides with preserved or enhanced biological activity when compared to the parent peptide HBD1 (3-11).

As an illustrative example, E (acidic amino acid) at position 8 could be substituted by R, (basic amino acid), F, I or P (non-polar, hydrophobic amino acids), or S (polar, uncharged amino acid), with all peptides mono-substituted at position 8 being biologically active on the osteoblast differentiation assay (see Table 12) Similar results were obtained by performing substitutions of amino acids 9 (P), 10, (K) and 11 (K) of the parent HBD1 (3-11) peptide (Tables 12 and 13).

Interestingly some substitutions generated peptides with increased potency when compared to the parent HBD1 (3-11) peptide. For example, substitution of K at position 11 by I, P or S resulted in peptides with 2 to 3 fold the potency of the parent HBD1 (3-11) peptide, substitution of K at position 10 by Q or Y resulted in peptides with 2 to 3 fold the potency of the parent HBD1 (3-11) peptide.

Poly-substitutions resulted in biologically active peptides. For example, the substitution of KK on positions 10 and 11 generated biologically active peptides (Tables 13 and 14). In particular, substitution of KK at positions 10 and 11 by FV, FQ, FN or VM resulted in peptides with about 3 fold the potency of the parent HBD1 (3-11) peptide (Table 14).

TABLE 12

Ability of HBD 1 fragments with amino-acid substitutions to stimulate differentiation of osteoblast cells (12 day interval)

| SEQ ID NO: | Peptide Sequence | Potency | Fold increase vs SEQ ID NO: 10 ± SE |
|---|---|---|---|
| 10 | HLGLEEPKK | + | 1 |
| 26 | HLGLERPKK | + | 1.11 |
| 27 | HLGLEFPKK | + | 1.58 ± 0.05 |
| 28 | HLGLEIPKK | + | 1.42 ± 0.13 |
| 29 | HLGLEPPKK | + | 1.95 ± 0.15 |
| 30 | HLGLESPKK | + | 1.40 ± 0.32 |
| 31 | HLGLEERKK | ± | 0.62 |
| 32 | HLGLEEFKK | ± | 0.58 |
| 33 | HLGLEELKK | + | 1.66 |
| 34 | HLGLEESKK | + | 1.06 |
| 35 | HLGLEEDKK | + | 1.26 |
| 36 | HLGLEEPFK | + | 1.23 ± 0.13 |
| 37 | HLGLEEPPK | + | 1.19 ± 0.2 |
| 38 | HLGLEEPSK | ++ | 2.01 ± 0.14 |
| 39 | HLGLEEPDK | + | 1.31 ± 0.08 |
| 40 | HLGLEEPKF | ++ | 2.33 ± 0.03 |
| 41 | HLGLEEPKI | ++ | 2.60 ± 0.56 |
| 42 | HLGLEEPKP | ++ | 2.67 ± 0.39 |
| 43 | HLGLEEPKS | ++ | 2.83 ± 0.09 |
| 44 | HLGLEEPKD | ++ | 2.60 ± 0.18 |

TABLE 13

Ability of HBD1 fragments with amino-acid substitutions to stimulate differentiation of osteoblast cells (15 day interval)

| SEQ ID NO: | Peptide Sequence | Potency | Fold increase vs DM ± SE |
|---|---|---|---|
| Control | DM | | 1 |
| 10 | HLGLEEPKK | + | 2.80 ± 0.13 |
| 45 | HLGLEEPIK | + | 2.27 ± 0.05 |
| 46 | HLGLEEPVK | + | 3.83 ± 1.75 |
| 47 | HLGLEEPQK | ± | 1.69 ± 0.20 |
| 48 | HLGLEEPTK | + | 4.65 ± 1.44 |

TABLE 13-continued

Ability of HBD1 fragments with amino-acid substitutions to stimulate differentiation of osteoblast cells (15 day interval)

| SEQ ID NO: | Peptide Sequence | Potency | Fold increase vs DM ± SE |
|---|---|---|---|
| 49 | HLGLEEPEK | ± | 1.72 ± 0.37 |
| 50 | HLGLEEPKH | + | 2.56 ± 1.09 |
| 51 | HLGLEEPKR | + | 2.45 ± 0.51 |
| 52 | HLGLEEPKL | + | 3.38 ± 0.19 |
| 53 | HLGLEEPKM | + | 4.03 ± 0.25 |
| 54 | HLGLEEPKW | ± | 1.54 ± 0.91 |
| 55 | HLGLEEPKV | + | 4.05 ± 0.50 |
| 56 | HLGLEEPKQ | + | 5.16 ± 0.34 |
| 57 | HLGLEEPKN | + | 3.58 ± 1.01 |
| 58 | HLGLEEPKY | + | 3.10 ± 0.08 |
| 59 | HLGLEEPKT | + | 2.38 ± 0.41 |
| 60 | HLGLEEPKE | + | 3.04 ± 0.62 |
| 61 | HLGLEEPSP | + | 3.48 ± 1.28 |
| 62 | HLGLEEPSS | + | 3.83 ± 0.28 |

TABLE 14

Ability of HBD1 fragments with amino-acid substitutions to stimulate differentiation of osteoblast cells (15 day interval)

| SEQ ID NO: | Peptide Sequence | Potency | Fold increase vs DM ± SE |
|---|---|---|---|
| Control | DM | | 1 |
| 10 | HLGLEEPKK | + | 2.90 ± 0.86 |
| 97 | HLGLEEPYK | ++ | 6.62 ± 1.92 |
| 98 | HLGLEEPQK | + | 4.14 ± 1.15 |
| 99 | HLGLEEPNK | ± | 1.46 ± 0.80 |
| 100 | HLGLEEPSF | ++ | 6.76 ± 1.32 |
| 101 | HLGLEEPSV | ++ | 6.32 ± 1.27 |
| 102 | HLGLEEPLM | + | 4.23 ± 0.93 |
| 103 | HLGLEEPLY | + | 2.33 ± 0.63 |
| 104 | HLGLEEPLN | - | 1.07 ± 0.20 |
| 105 | HLGLEEPLQ | - | 0.64 ± 0.22 |
| 106 | HLGLEEPFV | ++ | 6.98 ± 1.3 |
| 107 | HLGLEEPEQ | ++ | 7.74 ± 0.73 |
| 108 | HLGLEEPFN | ++ | 7.14 ± 2.20 |
| 109 | HLGLEEPVM | ++ | 6.54 ± 0.57 |
| 110 | HLGLEEPVN | + | 2.49 ± 0.93 |
| 111 | HLGLEEPMK | + | 4.79 ± 1.64 |

In these experiments, the effect of amino-acid substitutions on positions 3, 4, 5 and 6 of the parent HBD1 (3-11) peptide was also examined Each of the substituted peptides were synthesized and tested on the in vitro osteoblast differentiation assay. Results shown in Table 15 indicate that conservative or non-conservative substitutions yielded peptides with preserved or enhanced biological activity when compared to the parent peptide HBD1 (3-11).

TABLE 15

Ability of HBD1 fragments with amino-acid substitutions to stimulate differentiation of osteoblast cells (12 day interval)

| SEQ ID NO: | Peptide Sequence | Potency | Fold increase vs DM ± SE |
|---|---|---|---|
| Control | DM | | 1 |
| 10 | HLGLEEPKK | + | 3.19 ± 1.00 |
| 89 | KLGLEEPKK | + | 3.56 ± 1.91 |
| 90 | HVGLEEPKK | + | 2.40 ± 1.03 |
| 91 | HLPLEEPKK | + | 3.75 ± 1.60 |
| 92 | HLGIEEPKK | + | 2.70 ± 1.43 |
| 93 | NLGLEEPKK | + | 3.21 ± 1.56 |
| 94 | HTGLEEPKK | + | 3.01 ± 1.06 |
| 95 | HLKLEEPKK | + | 2.65 ± 0.72 |
| 96 | HLGSEEPKK | + | 3.15 ± 1.82 |

The effect of amino-acid substitutions at position 10 of a truncated HBD1 (3-11) peptide, notably HBD1 (3-10), was examined. The substituted peptides were synthesized and tested on the in vitro osteoblast differentiation assay. Results shown in Table 16 indicate that conservative substitution at position 10 of HBD1 (3-10) yielded peptides with enhanced biological activity when compared to the HBD1 (3-11) peptide. In particular, substitution of K at position 10 of HBD1 (3-10) resulted in peptides with about up to 3 fold the potency of the parent HBD1 (3-11)

TABLE 16

Ability of HBD1 fragments with amino-acid substitutions to stimulate differentiation of osteoblast cells (12 day interval)

| SEQ ID NO: | Peptide Sequence | Potency | Fold increase vs DM ± SE |
|---|---|---|---|
| Control | DM | | 1 |
| 10 | HLGLEEPKK | + | 2.90 ± 0.86 |

TABLE 16-continued

Ability of HBD1 fragments with amino-acid substitutions to stimulate differentiation of osteoblast cells (12 day interval)

| SEQ ID NO: | Peptide Sequence | Potency | Fold increase vs DM ± SE |
|---|---|---|---|
| 112 | HLGLEEPR | ++ | 5.84 ± 1.01 |
| 113 | HLGLEEPH | +++ | 8.90 ± 1.31 |

In conclusion, the substitution of amino acids at positions 3, 4, 5, 6, 8, 9, 10 and 11 of HBD1 (3-11) as well as the truncation of the amino acid at position 11 and the substitution of the amino acid at position 10 generated bioactive peptides, some of them being even more potent that HBD1 (3-11) itself. Mono-substitutions at the N-terminus or mono- or poly-substitutions at the C-terminus of the peptide with natural or non-natural amino-acids could therefore be a valid strategy to design potent analogs of HBD1 (3-11), the further design of analogs being performed according to common art by scientists skilled in the field of peptide chemistry.

Example 6: Effects of PEGylated HBD1 Fragment Analogs on Osteocalcin Expression During In Vitro Osteoblast Differentiation The peptide backbones were manufactured according to a standard manufacturing process in peptide chemistry by solid phase peptide synthesis (SPPS) using the Fmoc (9-fluorenylmethyloxycarbonyl) strategy (Merrifield, R. B. Solid phase peptide synthesis. I. The synthesis of a tetrapeptide. J. Am. Chem. Soc. 1963, 85, 2149-2154). Identity of peptides was verified by LC-MS. The purity (at least 95%) and the net peptide content of peptides were determined by RP-UPLC and elemental analysis, respectively.

Peptides were modified with 20 kDa mPEG-maleimide (NOF, Japan) coupled to a cysteine residue at either N- or C-terminus. The resulting crude mono-PEGylated peptide was purified on cation exchange column. Fractions containing the PEGylated peptides were pooled and diafiltered (using a polyethersulfane (PES) filter with a NMWL of 5,000 Da) with 0.9% Sodium chloride until conductivity was stable. The purified PEGylated peptides were analysed by MALDI-MS and RP-UPLC in order to determine the identity and the purity (at least 97%) of these modified peptides. The lack of unmodified peptides (unPEGylated peptides) was checked by SDS-PAGE. The PEGylated peptide concentrations were determined by UV.

Each peptide was tested in a biologic assay measuring its ability to stimulate differentiation of osteoblast cells over a 18-21 day interval as assessed by the stimulation of osteocalcin protein synthesis. MC-3T3 E1 clone 4 (CL4) osteoblast cells were obtained from ATCC (Manassas, Va., USA). Cells were cultured in α-MEM containing 10% fetal bovine serum (FBS; Thermo Fisher Scientific, Pittsburgh, Pa., USA). After confluency, culture medium was changed to differentiation medium (DM), which contained 10% FBS plus 50 µg/mL ascorbic acid and 4 mM β-glycerol phosphate, with or without a test peptide (2 µg/mL). Fresh DM, with or without test peptide, was applied every 72 hours. The cell monolayers were lysed in a modified radioimmunoprecipitation assay (RIPA) buffer. Total cellular protein in the lysates was determined using BCA (Thermo Fisher Scientific, Rockford, Ill., USA). Cell proteins are separated on SDS-PAGE gel and transferred on PVDF membrane for analysis. Osteocalcin detection was performed using anti-osteocalcin antibody at 1:200 dilution (Santa Cruz Biotechnology, Inc, Santa Cruz, Calif., USA) and visualized using enhanced chemiluminescence (Thermo Fisher Scientific, Rockford, Ill., USA).

In these experiments, the effect of the conjugation of HBD1 (3-11), HBD1 (1-13), or HBD1 (2-11) with a Poly-EthyleneGlycol (PEG) chain was examined. Each of the PEGylated peptides were synthesized conjugated and tested on the in vitro osteoblast differentiation assay. As shown in Table 17, PEGylation of the peptides (9, 10 or 13 amino acids in length) with a PEG20 at the N-terminus side of the peptide generated compounds with similar activity to that of the parent unconjugated peptide HBD1 (1-13). Interestingly, conjugation of PEG20 at the C-terminus of the 13 amino acid peptide HBD1 (1-13) or of the 10 amino acid peptide HBD1 (2-11) appeared to increase the in vitro biological potency.

TABLE 17

Ability of PEGylated HBD1 fragments to stimulate differentiation of osteoblast cells

| SEQ ID NO: | Peptide Sequence | Potency | Fold increase vs DM ± SE |
|---|---|---|---|
| 1 | KHHLGLEEPKKLR | + | 1 |
| 63 | PEG20-C-KHHLGLEEPKKLR | + | 1.4 ± 0.3 |
| 64 | KHHLGLEEPKKLR-C-PEG20 | ++ | 2.2 ± 0.4 |
| 65 | PEG20-C-HHLGLEEPKK | + | 1.4 ± 0.1 |
| 66 | HHLGLEEPKK-C-PEG20 | ++ | 2.2 ± 0.2 |
| 67 | PEG20-C-HLGLEEPKK | + | 1.9 ± 0.2 |

In conclusion, PEGylation of the peptides of the present disclosure may be a suitable conjugation method to improve pharmacokinetic profile while preserving or enhancing in vitro biological activity.

Example 7: Effects of Acylated HBD1 Fragment Analogs on Osteocalcin Expression During In Vitro Osteoblast Differentiation The peptides were manufactured according to a standard manufacturing process in peptide chemistry by solid phase peptide synthesis (SPPS) using the Fmoc (9-fluorenylmethyloxycarbonyl) strategy (Merrifield, R. B. Solid phase peptide synthesis. I. The synthesis of a tetrapeptide. J. Am. Chem. Soc. 1963, 85, 2149-2154). Identity of peptides was verified by LC-MS. The purity (at least 95%) and the net peptide content of peptides were determined by RP-UPLC and elemental analysis, respectively.

Each acylated peptide was tested in a biologic assay measuring its ability to stimulate differentiation of osteoblast cells over a 18-21 day interval as assessed by the stimulation of osteocalcin protein synthesis. MC-3T3 E1 clone 4 (CL4) osteoblast cells were obtained from ATCC (Manassas, Va., USA). Cells were cultured in α-MEM containing 10% fetal bovine serum (FBS; Thermo Fisher Scientific, Pittsburgh, Pa., USA). After confluency, culture medium was changed to differentiation medium (DM), which contained 10% FBS plus 50 µg/mL ascorbic acid and 4 mM β-glycerol phosphate, with or without a test peptide (1 µg/L). Fresh DM, with or without test peptide, was applied every 72 hours. The cell monolayers were lysed in a modified radioimmunoprecipitation assay (RIPA) buffer. Total cellular protein in the lysates was determined using BCA (Thermo Fisher Scientific, Rockford, Ill., USA). Cell proteins are separated on SDS-PAGE gel and transferred on PVDF membrane for analysis. Osteocalcin detection was performed using anti-osteocalcin antibody at 1:200 dilution (Santa Cruz Biotechnology, Inc, Santa Cruz, Calif., USA) and visualized using enhanced chemiluminescence (Thermo Fisher Scientific, Rockford, Ill., USA).

In these experiments, the effect of the conjugation of the HBD1 (3-11) peptide or of the HBD1 (2-11) peptide with an acyl chain of various lengths was examined. Each of the acylated peptides were synthesized and tested on the in vitro osteoblast differentiation assay. As shown in Table 18, acylation of the peptides (9 or 10 amino acids in length) with 14 to 20 carbon chains (C14 to C20) at the N-terminus side of the peptide generated compounds with similar activity to that of the parent unacylated peptides (HBD1 (3-11) and HBD1 (2-11)). Acylation at the C-terminus end did not appear to change the in vitro biological activity.

TABLE 18

Ability of Acylated HBD1 fragments to stimulate differentiation of osteoblast cells

| SEQ ID NO: | Peptide Sequence | Potency | Fold increase vs DM ± SE |
|---|---|---|---|
| Ccontrol | DM | | 1 |
| 16 | HHLGLEEPKK | + | 3.28 ± 0.36 |
| 68 | C16:0-HHLGLEEPKK | + | 2.52 ± 0.52 |
| 69 | C18:0-HHLGLEEPKK | + | 2.48 ± 0.27 |
| 70 | C20:0-HHLGLEEPKK | + | 2.11 ± 0.11 |
| 10 | HLGLEEPKK | + | 2.51 ± 0.42 |
| 71 | C14:0-HLGLEEPKK | + | 1.98 ± 0.22 |
| 72 | C16:0-HLGLEEPKK | + | 3.21 ± 0.49 |
| 73 | C18:0-HLGLEEPKK | + | 2.93 ± 0.16 |
| 74 | C20:0-HLGLEEPKK | + | 5.05 ± 0.95 |
| 75 | C16:0-diacid-HLGLEEPKK | + | 3.39 ± 0.19 |
| 76 | HLGLEEPKK-C16:0 | + | 3.18 ± 0.31 |

In a separate experiment, the effect of cyclization was examined on of the HBD1 (3-11) peptide. The cyclic HBD1 (3-11) was synthetized and tested on the in vitro osteoblast differentiation assay. Cyclization did not appear to change the in vitro biological activity.

In conclusion, acylation or cyclization of the peptides of the present disclosure may be a suitable method to improve pharmacokinetic profile while preserving the in vitro biological activity.

Example 8: Effects of Various Doses of HBD1 Fragment Analogs on Osteocalcin Expression During In Vitro Osteoblast Differentiation Peptides were manufactured according to a standard manufacturing process in peptide chemistry by solid phase peptide synthesis (SPPS) using the Fmoc (9-fluorenylmethyloxycarbonyl) strategy (Merrifield, R. B. Solid phase peptide synthesis. I. The synthesis of a tetrapeptide. J. Am. Chem. Soc. 1963, 85, 2149-2154). Identity of the peptides was verified by LC-MS. The purity (at least 95%) and the net peptide content of peptides were determined by RP-HPLC and elemental analysis, respectively.

The peptides were tested at different concentrations in a biologic assay measuring their ability to stimulate differentiation of osteoblast cells over a 18 day interval as assessed by the stimulation of osteocalcin protein synthesis. MC-3T3 E1 clone 4 (CL4) osteoblast cells were obtained from ATCC (Manassas, Va., USA). Cells were cultured in α-MEM containing 10% fetal bovine serum (FBS; Thermo Fisher Scientific, Pittsburgh, Pa., USA). After confluency, culture medium was changed to differentiation medium (DM), which contained 10% FBS plus 50 µg/mL ascorbic acid and 4 mM β-glycerol phosphate, with or without an ascending dose of the peptide. Fresh DM, with or without the peptide, was applied every 72 hours. The cell monolayers were lysed in a modified radioimmunoprecipitation assay (RIPA) buffer. Total cellular protein in the lysates was determined using BCA (Thermo Fisher Scientific, Rockford, Ill., USA). Cell proteins are separated on SDS-PAGE gel and transferred on PVDF membrane for analysis. Osteocalcin detection was performed using anti-osteocalcin antibody at 1:200 dilution (Santa Cruz Biotechnology, Inc, Santa Cruz, Calif., USA) and visualized using enhanced chemiluminescence (Thermo Fisher Scientific, Rockford, Ill., USA). The results of this experiment are summarized in Tables 19 and 20 below.

In this experiment an acylated HBD1 (3-11) fragment, a HBD1 (3-11) fragment with amino acid substitutions at the C-terminus, as well as truncated HBD1 (3-11) fragment with an amino acid substitution at the C-terminus (i.e., HBD1 (3-10) with an amino acid substitution at the C-terminus), as identified in Tables 19, 20 and 21, were tested at several doses in the osteoblast differentiation assay. The results show that these peptides improved osteoblast differentiation in a dose-dependent fashion, exhibiting high potency at the highest doses tested. This suggests a therapeutic potential for acylated HBD1 (3-11), for C-terminal analogs of HBD1 (3-11) and for C-terminal analogs of HBD1 (3-10) in bone disorders.

TABLE 19

Ability of various doses of acylated HBD1 (3-11) to stimulate differentiation of osteoblast cells

| SEQ ID NO: | Peptide Sequence | Dose (µM) | Fold increase vs DM ± SE |
|---|---|---|---|
| Control | DM | | 1 |
| 10 | HLGLEEPKK | 1.0 | 2.65 ± 0.49 |
| 73 | C18:0-HLGLEEPKK | 1.0 | 3.46 ± 0.47 |
| 73 | | 2.0 | 4.48 ± 0.07 |
| 73 | | 3.0 | 5.66 ± 0.45 |

TABLE 20

Ability of various doses of HBD1 (3-11) analogs to stimulate differentiation of osteoblast cells

| SEQ ID NO: | Peptide Sequence | Dose (µM) | Fold increase vs DM ± SE |
|---|---|---|---|
| Control | DM | | 1 |
| 10 | HLGLEEPKK | 0.25 | 1.24 ± 0.11 |

TABLE 20-continued

Ability of various doses of HBD1 (3-11) analogs to stimulate differentiation of osteoblast cells

| SEQ ID NO: | Peptide Sequence | Dose (μM) | Fold increase vs DM ± SE |
|---|---|---|---|
| 10 | HLGLEEPKK | 0.5 | 2.43 ± 0.49 |
| 10 | HLGLEEPKK | 1.0 | 3.32 ± 0.55 |
| 108 | HLGLEEPFN | 0.25 | 3.7 ± 0.47 |
| 108 | HLGLEEPFN | 0.5 | 4.80 ± 1.12 |
| 108 | HLGLEEPFN | 1.0 | 6.20 ± 1.64 |

TABLE 21

Ability of various doses of a HBD1 (3-10) analog to stimulate differentiation of osteoblast cells

| SEQ ID NO: | Peptide Sequence | Dose (μM) | Fold increase vs DM ± SE |
|---|---|---|---|
| Control | DM | | 1 |
| 10 | HLGLEEPKK | 0.25 | 1.23 ± 0.16 |
| 10 | HLGLEEPKK | 0.5 | 2.34 ± 0.45 |
| 10 | HLGLEEPKK | 1.0 | 3.34 ± 0.45 |
| 113 | HLGLEEPH | 0.25 | 2.99 ± 0.53 |
| 113 | HLGLEEPH | 0.5 | 3.83 ± 1.64 |
| 113 | HLGLEEPH | 1.0 | 4.67 ± 0.46 |

Example 9: Stability of HBD1 Fragments in Human Plasma

The peptides HBD1 (1-13), HBD1 (3-11), cyclic HBD1 (3-11), HBD1 (1-13) with palmitic acid at the N-terminus (C16:0), HBD1 (3-11) with palmitic acid at the N-terminus (C16:0)) and HBD1 (3-11) with stearic acid at the N-terminus (C18:0) were manufactured according to a standard manufacturing process in peptide chemistry by solid phase peptide synthesis (SPPS) using the Fmoc (9-fluorenylmethyloxycarbonyl) strategy (Merrifield, R. B. Solid phase peptide synthesis. I. The synthesis of a tetrapeptide. J. Am. Chem. Soc. 1963, 85, 2149-2154). Identity of peptides was verified by LC-MS. The purity (at least 95%) and the net peptide content of peptides were determined by RP-HPLC and elemental analysis, respectively.

The peptides were spiked at 1 μg/mL (peptide backbone) into pre-warmed human K$_2$EDTA plasma (at 37° C.) and incubated for up to 48 hours. Aliquots of plasma were extracted at specific time points (0, 24 and 48 hours post spike). Extraction was performed with acetonitrile:water (75:25, v/v) for HBD1 (1-13), HBD1 (1-13) with palmitic acid at the N-terminus (C16:0), HBD1 (3-11) with palmitic acid at the N-terminus (C16:0)) and HBD1 (3-11) with stearic acid at the N-terminus (C18:0) or with acetonitrile:water:formic acid (75:25:0.1, v/v/v) for HBD1 (3-11) and cyclic HBD1 (3-11). The peptides were analyzed using developed LC (C18 reverse phase column)—positive ion electrospray MS/MS methods specific to each peptide. The peak area at each time point was expressed as a percentage of the value obtained for the t=0 minutes time point. The results are provided in Table 22.

TABLE 22

Stability of HBD1 fragments in human plasma

| SEQ ID NO: | Peptide sequence | Remaining parent peptide in human plasma | |
|---|---|---|---|
| | | 24 hours post spike | 48 hours post spike |
| 1 | KHHLGLEEPKKLR | 29% | 18% |
| 78 | C16:0-KHHLGLEEPKKLR | 58% | 52% |
| 10 | HLGLEEPKK | 92% | 87% |
| 77 | Cyclic (HLGLEEPKK) | 98% | 95% |
| 72 | C16:0-HLGLEEPKK | 94% | 87% |
| 73 | C18:0-HLGLEEPKK | 89% | 91% |

The data provided above show that HBD1 (1-13) was markedly degraded in human plasma (29% and 18% remaining parent peptide after 24 and 48 hours incubation at 37° C., respectively). The N-terminal acylation of HBD1 (1-13) with palmitic acid (SEQ ID NO: 78) markedly improved the stability of the parent peptide (52% versus 18% remaining parent peptide after 48 hours incubation at 37° C.). This result indicates that acylation at the N-terminus protects this peptide against peptidase degradation in human plasma. Surprisingly, a shorter 9 amino acids peptide HBD1 (3-11) was very stable in human plasma with minor degradation detected after 24 and 48 hours incubation at 37° C. (92% and 87% remaining parent peptide, respectively). Cyclic and N-terminal acylated HBD1 (3-11) (with palmitic or stearic acid) (SEQ ID NOs: 77, 72 and 73 respectively) had a plasma stability profile similar to that of the corresponding unconjugated linear peptide HBD1 (3-11).

As previously mentioned herein, it is known by people skilled in the art of developing peptides that the degradation of peptides in human plasma is a major issue limiting their use as therapeutic agents. Degradation in human plasma markedly decreases the therapeutic exposure, thus efficacy. In this context, the unexpected observation that the 9 amino acid-long sequence HBD1 (3-11) is both stable in human plasma and biologically active (see results from Example 1) is a relevant improvement versus the previously described 13 amino acid-long peptide HBD1 (1-13).

In addition, both cyclisation and N-terminus acylation of the 13 and the 9 amino acid peptides allowed to yield new compounds that were both biologically active and stable in human plasma.

Example 10: Pharmacokinetic of HBD1 Fragments in Male Sprague Dawley Rats after Intravenous and Subcutaneous Injection HBD1 (1-13), HBD1 (3-11), cyclic HBD1 (3-11), HBD1 (3-11) with palmitic acid at the N-terminus (C16:0) and HBD1 (3-11) with stearic acid at the N-terminus (C18:0) were manufactured according to a standard manufacturing process in peptide chemistry by solid phase peptide synthesis (SPPS) using the Fmoc (9-fluorenylmethyloxycarbonyl) strategy (Merrifield, R. B. Solid phase peptide synthesis. I. The synthesis of a tetrapeptide. J. Am. Chem. Soc. 1963, 85, 2149-2154). Identity of peptides was verified by LC-MS.

The purity (at least 95%) and the net peptide content of peptides were determined by RP-HPLC and elemental analysis, respectively.

The peptides were reconstituted in saline (0.9% NaCl). Three male Sprague Dawley rats were used per group. Intravenous doses were administered into a lateral tail vein at the dose of 1 μmol net peptide/kg. Subcutaneous doses were administered into the right flank of each animal, also at the dose of 1 μmol net peptide/kg. Following dosing, serial whole blood samples (ca. 0.25 mL) were collected from a lateral tail vein into $K_2EDTA$ treated containers. Following each blood sample collection, samples were placed into a cooling block at 4° C. Samples were collected prior to dosing then at 2, 5, 15 and 30 minutes then 1, 2, 4, 6 and 8 and 24 hours post dose for intravenous injection and at 15 and 30 minutes then 1, 2, 4, 6, 8 and 24 hours post dose for subcutaneous injection.

Blood samples were centrifuged at 10000×g for 2 minutes at 4° C. and resultant plasma aspirated off into clean fully, labelled tubes. Plasma samples were snap frozen following aspiration then stored at −80° C. Peptides were extracted and analyzed as described in Example 9. The limits of quantification of these methods were 0.001 nmol/mL for cyclic HBD1 (3-11) and HBD1 (3-11) and 0.003 nmol/mL for HBD1 (1-13). All values below these limits of quantification were considered as zero.

Figure 2:
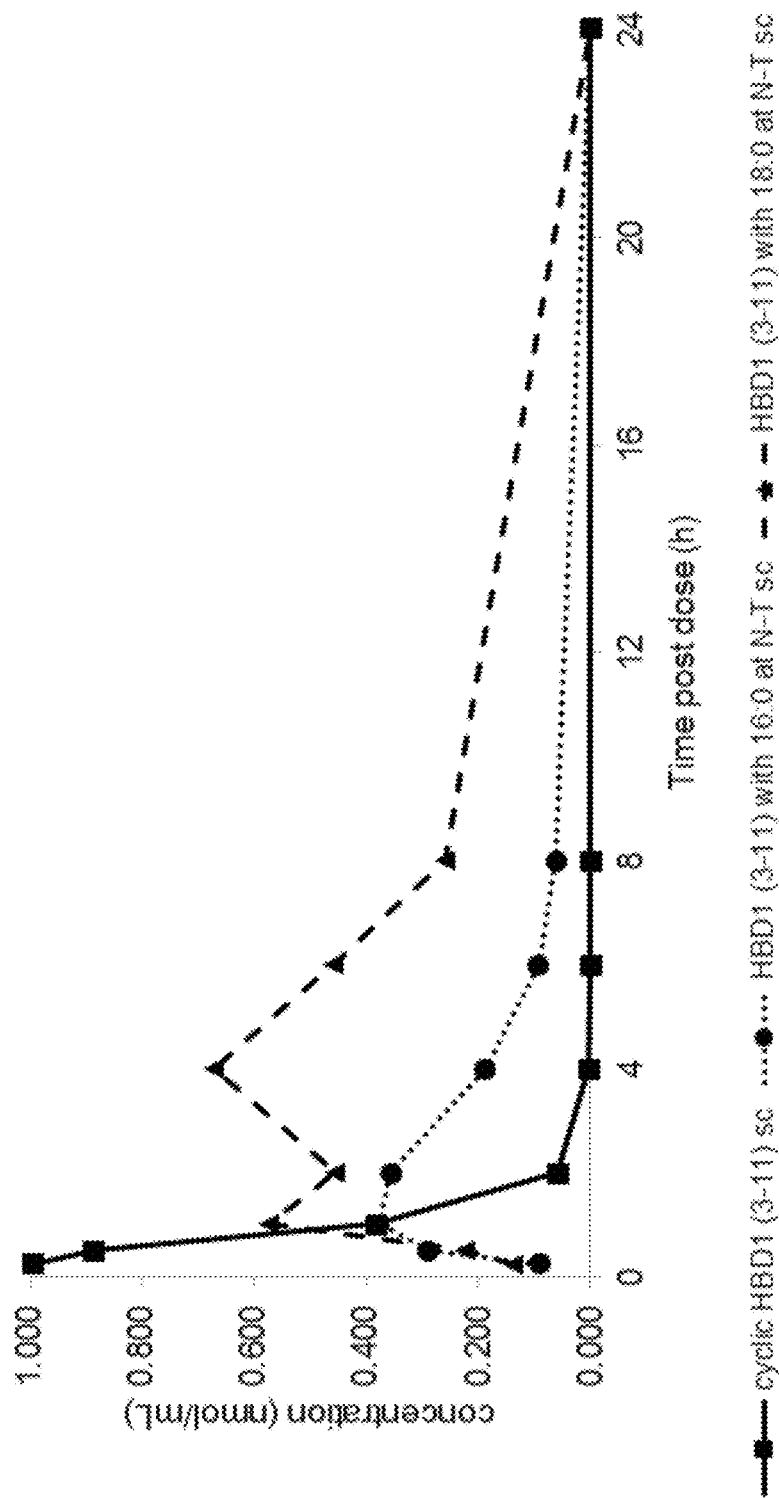
FIG. 2 is a graph showing the pharmacokinetic profile of peptides according to some embodiments of the present technology in male Sprague Dawley rats after subcutaneous injection of cyclic HBD1 (3-11), HBD1 (3-11) with C16:0 at N-terminal, HBD1 (3-11) with C18:0 at N-terminal.

Animals dosed with HBD1 (1-13) and HBD1 (3-11) showed no quantifiable exposure after administration by either dose route, therefore no pharmacokinetic parameters could be calculated for these two peptides. Interestingly, as shown in FIGS. 1 and 2, cyclic HBD1 (3-11) administration resulted in detectable plasma levels for up to 8 hours and 4 hours after intravenous and subcutaneous administration respectively and all HBD1 (3-11) with palmitic acid at the N-terminus (C16:0) and HBD1 (3-11) with stearic acid at the N-terminus (C18:0) dosed animals showed exposure up to 8 hours by either dose routes. FIGS. 1 and 2 illustrate graphs showing the pharmacokinetic profiles of cyclic HBD1 (3-11), HBD1 (3-11) with palmitic acid at the N-terminus (C16:0) and HBD1 with stearic acid at the N-terminus (C18:0) after single intravenous and subcutaneous injection in Sprague Dawley rats respectively. Individual values represent the mean of the values obtained for three different rats. The pharmacokinetic parameters for cyclic HBD1 (3-11), HBD1 (3-11) with palmitic acid at the N-terminus (C16:0) and HBD1 (3-11) with stearic acid at the N-terminus (C18:0) after intravenous (iv) and subcutaneous (sc) injection are summarized in Table 23.

TABLE 23

Pharmacokinetic parameters of HBD1 fragments in male Sprague Dawley rats

|  | Cyclic HBD1 (3-11) | | HBD1 (3-11) with palmitic acid at the N-terminus (C16:0) | | HBD1 (3-11) with stearic acid at the N-terminus (C18:0) | |
| --- | --- | --- | --- | --- | --- | --- |
|  | iv | Sc | iv | Sc | iv | Sc |
| $C_{max}$ (nmol/mL) | 5.72 | 1.06 | 7.89 | 0.41 | 10.24 | 0.54 |
| $T_{max}$ (h) | 0.033 | 0.25 | 0.033 | 1.000 | 0.033 | 4.000 |
| $AUC_{0-t}$ (h*nmol/mL) | 2.09 | 0.99 | 4.46 | 1.57 | 9.28 | 4.81 |
| $T_{last}$ (h) | 8 | 4 | 8 | 8 | 8 | 8 |
| F (%) |  | 48 |  | 35 |  | 52 |

$T_{last}$ correspond to the last time point with detectable peptide

The data provided above shows that cyclic HBD1 (3-11) rapidly diffuse from the subcutaneous site of injection to the blood. Interestingly, HBD1 (3-11) with stearic acid at the N-terminus (C18:0) showed better intravenous and subcutaneous exposure and bioavailability in rats than HBD1 (3-11) with palmitic acid at the N-terminus (C16:0) and cyclic HBD1 (3-11) (9.28 vs 4.46 and 2.09 h*nmol/mL for iv injection, 4.81 vs 1.57 or 0.99 h*nmol/mL for sc injection, and 52 vs 35 and 48% respectively).

In conclusion, these results show that cyclisation or acylation of the 9 amino acid-long peptide yielded peptides (i.e., cyclic HBD1 (3-11) or HBD1 (3-11) with palmitic acid at the N-terminus (C16:0) and HBD1 (3-11) with stearic acid at the N-terminus (C18:0)) with improved pharmacokinetic properties when compared to the linear peptide HBD1 (3-11). The cyclisation or the acylation of the peptides of the present disclosure may allow to improve their therapeutic potential.

Example 11: Pharmacokinetic of Acylated HBD-1 Fragment Analogs in Male Sprague Dawley Rats after Subcutaneous Injection HBD1 (1-13) with palmitic acid at the N-terminus (C16:0), HBD1 (3-11) with palmitic acid at the N-terminus (C16:0), HBD1 (3-11) with myristic acid at the N-terminus (14:0), HBD1 (3-11) with stearic acid at the N-terminus (C18:0), HBD1 (3-11) with arachidic acid at the N-terminus (C20:0), HBD1 (3-11) with palmitic diacid at the N-terminus (C16:0-diacid), HBD1 (3-11) with palmitic acid at the C-terminus (C16:0) were manufactured according to a standard manufacturing process in peptide chemistry by solid phase peptide synthesis (SPPS) using the Fmoc (9-fluorenylmethyloxycarbonyl) strategy (Merrifield, R. B. Solid phase peptide synthesis. I. The synthesis of a tetrapeptide. J. Am. Chem. Soc. 1963, 85, 2149-2154). Identity of peptides was verified by LC-MS. The purity (at least 95%) and the net peptide content of peptides were determined by RP-HPLC and elemental analysis, respectively.

Figure 3:
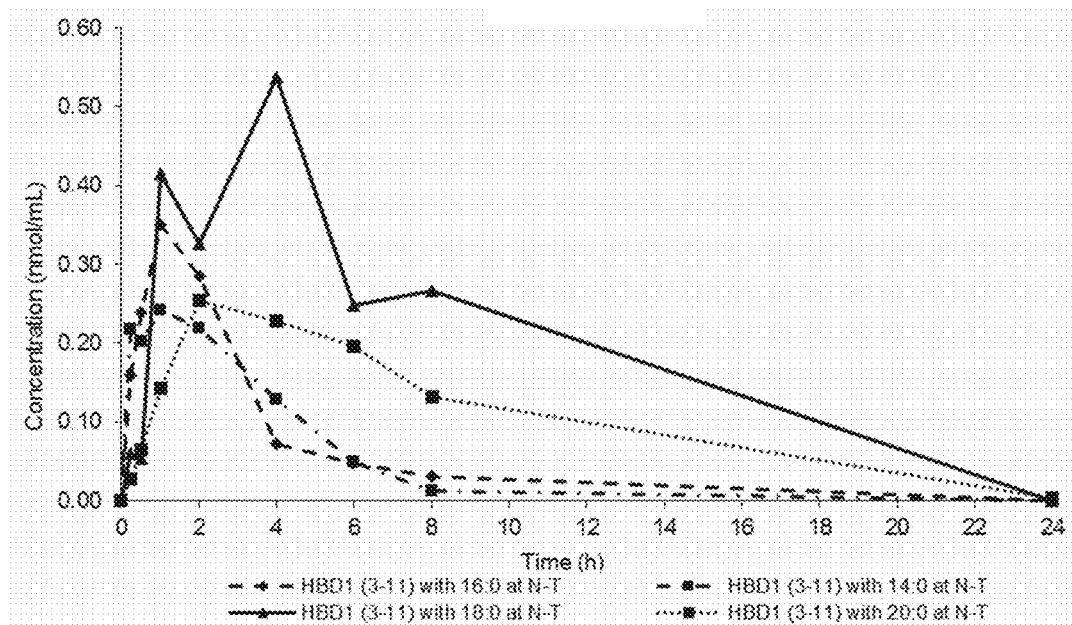
FIG. 3 is a graph showing the pharmacokinetic profile of peptides according to some embodiments of the present technology in male Sprague Dawley rats after subcutaneous injection of HBD1 (3-11) with C16:0 at N-terminal, HBD1 (3-11) with C14:0 at N-terminal, HBD1 (3-11) with C18:0 at N-terminal and HBD1 (3-11) with C20:0 at N-terminal.

The peptides were reconstituted in saline (0.9% NaCl). Three male Sprague Dawley rats (approximately 6 weeks of age) were used per group. Subcutaneous doses were administered into the right flank of each animal at the target dose level of 1 μmol net peptide/kg. Following dosing, serial whole blood samples (ca. 0.3 mL) were collected from retro-orbital sinus into $K_2EDTA$ treated containers. Following each blood sample collection, samples were placed into a cooling block at 4° C. Samples were collected prior to dosing then at 15 and 30 minutes then 1, 2, 4, 6, 8 and 24 hours post dose for subcutaneous injection. Blood samples were centrifuged at 3500×rpm for 10 minutes at 4° C. and resultant plasma aspirated off into clean fully, labelled tubes. Plasma samples were snap frozen following aspiration then stored at −80° C. The peptides were extracted with acetonitrile:water (75:25, v/v) and analyzed using developed LC-MS/MS methods as described in Example 9. The limits of detection of these methods are 0.003 nmol/mL for HBD1 (1-13) with palmitic acid at the N-terminus (C16:0), 0.0008 nmol/mL for HBD1 (3-11) with palmitic acid at the N-terminus (C16:0), 0.0070 nmol/mL for HBD1 (3-11) with stearic acid at the N-terminus (C18:0), and 0.0015 nmol/mL for HBD1 (3-11) with myristic acid at the N-terminus (C14:0), HBD1 (3-11) with arachidic acid at the N-terminus (C20:0), HBD1 (3-11) with palmitic diacid at the N-terminus (C16:0-diacid), HBD1 (3-11) with palmitic acid at the C-terminus (C16:0). All values below these limits of quantification were considered as zero. The pharmacokinetic parameters for each peptide after subcutaneous injection are summarized in Table 24. PK profile of some of these peptides are shown in FIG. 3.

Interestingly, as shown in Table 24, peptide administration resulted in significant plasma levels for up to 8 hours after subcutaneous administration whatever the acylated peptide tested.

kg. Subcutaneous doses were administered into the right flank of each animal, also at the dose of 0.5 µmol net peptide/kg. Following dosing, serial whole blood samples (ca. 0.25 mL) were collected from a jugular vein into $K_2EDTA$ treated containers. Following each blood sample collection, samples were placed into a cooling block at 4° C. Samples were collected prior to dosing then at 5 and 30

TABLE 24

Pharmacokinetic parameters of acylated HBD-1 analogs in male Spraque Dawley rats

| SEQ ID NO: | Peptide sequence | $C_{max}$ (nmol/mL) | $T_{max}$ (h) | $AUC_{0-t}$ (h*nmol/mL) | $T_{last}$ (h) |
|---|---|---|---|---|---|
| 78 | C16:0-KHHLGLEEPKKLR | 0.01 | 6.00 | 0.01 | 8 |
| 71 | C14:0-HLGLEEPKK | 0.24 | 1.00 | 1.11 | 6 |
| 72 | C16:0-HLGLEEPKK | 0.35 | 1.00 | 1.34 | 8 |
| 73 | C18:0-HLGLEEPKK | 0.54 | 4.00 | 4.81 | 8 |
| 74 | C20:0-HLGLEEPKK | 0.25 | 2.00 | 2.58 | 8 |
| 75 | C16:0-diacid-HLGLEEPKK | 0.58 | 0.25 | 1.14 | 8 |
| 76 | HLGLEEPKK-C16:0 | 0.50 | 0.25 | 1.09 | 8 |

$T_{last}$ correspond to the last time point with detectable peptide

The data from Table 24 and FIG. 3 show that higher peptide exposure was obtained with HBD1 (3-11) with stearic acid at the N-terminus (C18:0). The use of longer acyl chain conjugated to the peptide increases the exposure of the corresponding acylated peptide due most likely to a stronger interaction with serum proteins (e.g., albumin) But interestingly, HBD1 (3-11) with arachidic acid at the N-terminus (C20:0) has a lower exposure than HBD1 (3-11) with stearic acid at the N-terminus (C18:0) possibly due to a lower bioavailability of this peptide after subcutaneous injection.

In conclusion, HBD1 (3-11) with stearic acid at the N-terminus (C18:0) is biologically active, stable in human plasma and has a bioavailability and exposure in rat that are enhanced vs the unacylated HBD1 peptide and other acylated peptides. Thus HBD1 (3-11) with stearic acid at the N-terminus (C18:0) could be a potential drug candidate in human as a bone anabolic drug with a suitable regimen of administration, such as for example a once-a-day subcutaneous administration.

Example 12: Pharmacokinetic of HBD1 Fragments in Göttingen Minipigs after Intravenous and Subcutaneous Injection HBD1 (3-11) with stearic acid at the N-terminus (C18:0) was manufactured according to a standard manufacturing process in peptide chemistry by solid phase peptide synthesis (SPPS) using the Fmoc (9-fluorenylmethyloxycarbonyl) strategy (Merrifield, R. B. Solid phase peptide synthesis. I. The synthesis of a tetrapeptide. J. Am. Chem. Soc. 1963, 85, 2149-2154). Identity of the peptide was verified by LC-MS. The purity (at least 95%) and the net peptide content was determined by RP-HPLC and elemental analysis, respectively.

The peptide was reconstituted in saline (0.9% NaCl). Three Göttingen minipigs (approximately 8-10 months of age) were used per group. Intravenous doses were administered into an ear vein at the dose of 0.5 µmol net peptide/ minutes then 1, 2, 4, 8, 25, 48, 72 and 96 hours post dose for intravenous injection and at 15 and 30 minutes then 1, 2, 4, 8, 25, 48, 72 and 96 hours post dose for subcutaneous injection.

Figure 4:
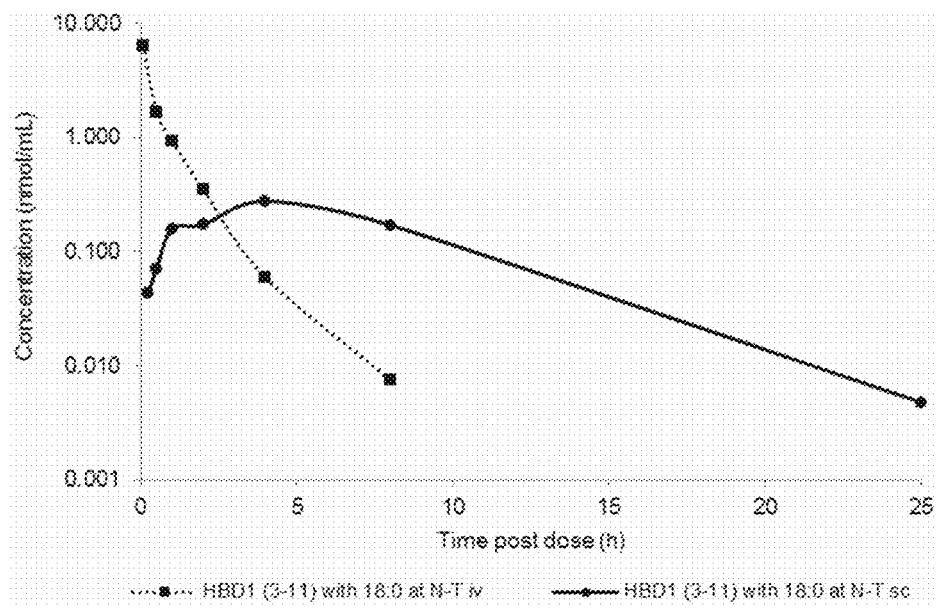
FIG. 4 is a graph showing the pharmacokinetic profile of peptides according to some embodiments of the present technology after single intravenous (iv) and subcutaneous (sc) injection in Göttingen minipigs of HBD1 (3-11) with C18:0 at N-terminal. Individual values represent the mean of the values obtained for three different subjects.

Blood samples were centrifuged at 10000×g for 2 minutes at 4° C. and resultant plasma aspirated off into clean fully, labelled tubes. Plasma samples were snap frozen following aspiration then stored at −80° C. Peptide extraction and analysis were performed as described in Example 9. The limit of quantification of this method is 0.0015 nmol/mL. All values below this limit of quantification are considered as zero. The results are presented in FIG. 4.

Following 0.5 µmol/kg administration of the peptide to Göttingen minipigs, maximum concentrations ($C_{max}$) with means of 6.27 and 0.29 nmol/mL, times post dose for maximum concentration ($T_{max}$) with medians of 0.083 and 4 hours and mean total exposure ($AUC_{0-4}$) values of 3.752 and 3.072 h*nmol/mL were observed after intravenous and subcutaneous injection respectively. The mean calculated subcutaneous bioavailability relative to i.v. was 83.1%.

Interestingly all HBD1 (3-11) with stearic acid at the N-terminus (C18:0) dosed Göttingen minipigs showed exposure up to 25 hours after subcutaneous administration, longer exposure than in rats (refer to Example 9). This result strongly suggests that subcutaneous daily dosing of HBD1 (3-11) with stearic acid at the N-terminus (C18:0) in human should be sufficient for at least a full day exposure of the product.

Example 13: HBD1 Fragment Induces Bone Formation in Ovariectomized Rat

HBD1 (3-11) with stearic acid at the N-terminus (C18:0) was manufactured according to a standard manufacturing process in peptide chemistry by solid phase peptide synthesis (SPPS) using the Fmoc (9-fluorenylmethyloxycarbonyl) strategy (Merrifield, R. B. Solid phase peptide synthesis. I. The synthesis of a tetrapeptide. J. Am. Chem. Soc. 1963, 85, 2149-2154). Identity of the peptide was verified by LC-MS. The purity (at least 95%) and the net peptide content was determined by RP-HPLC and elemental analysis, respectively.

Effects on bone of three doses of HBD1 (3-11) with stearic acid at the N-terminus (C18:0) analog were tested in vivo in ovariectomized (OVX) rats, a recognized model for human osteoporosis, in particular postmenopausal osteoporosis. Each group included ten female Sprague-Dawley rats that were four months of age at the beginning of the in-life phase of the study. Treatment started six weeks after OVX surgery and lasted for six additional weeks. Groups were randomized before surgery according to body weight and tibial metaphysis Bone Mineral Density (BMD) as measured by peripheral quantitative computed tomography (pQCT) from Norland Stratec XCT Research SA equipment (Norland Stratec Medizintechnik, Birkenfeld, Germany).

The peptide was reconstituted in saline solution (0.9% NaCl) and administered subcutaneously twice a day at the doses of 0.8 mg/kg (low), 1.6 mg/kg (med) or 3.2 mg/kg (high) in a volume of 1 mL/kg. The control group was administered twice a day with saline by s.c. administration. Rats were weighed once a week and the volume of dosing solution administered was adjusted accordingly.

Figure 5A:
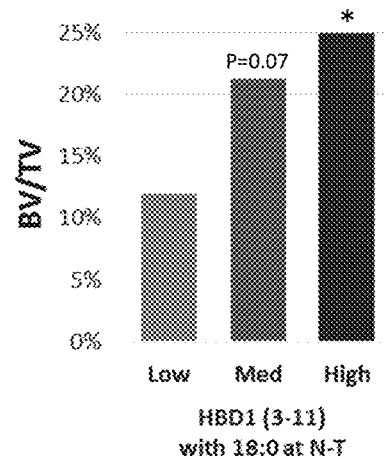
FIGS. 5A-5C are graphs showing the effect of peptides according to some embodiments of the present technology on bone in ovariectomized rat. The graphs show the percent increase from OVX vehicle in selected μCT parameters from tibial metaphysis after 6-week HBD1 (3-11) with C18:0 at N-terminal treatment in OVX Sprague-Dawley rats.
Figure 5B:
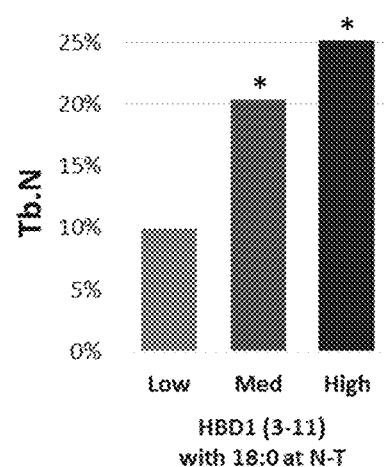
Figure 5C:
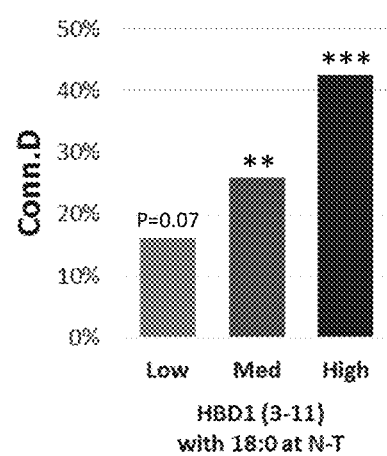

High-resolution micro-computed tomography (µCT) measurements using Sky Scan 1072 or 1172 High Resolution Scanner (Bruker microCT, Kontich, Belgium) were performed ex vivo in right proximal tibia at the end of the treatment period for measuring bone volume, bone cross-sectional dimensions and bone microarchitecture. FIGS. 5A, 5B and 5C show the percent increase from OVX animals HBD1 (3-11) with stearic acid at the N-terminus (C18:0) groups for following selected parameters: Bone Volume Fraction (BV/TV; %), Trabecular number (Tb.N; mm$^{-1}$) and Connectivity Density (Conn.D; mm$^{-3}$).

Figure 6A:
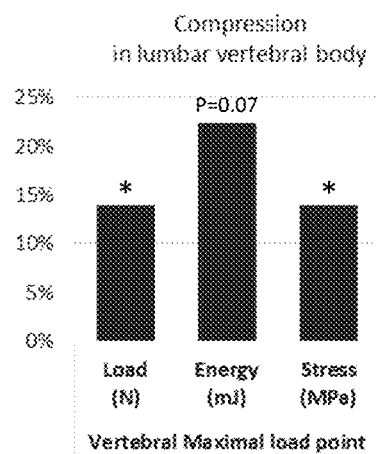
FIGS. 6A-6B are graphs showing the effect of the peptides according to some embodiments of the present technology on the indicated bone biomechanical properties. The graphs show the percent increase from OVX vehicle in selected biomechanical parameters from Lumbar vertebrae (FIG. 6A) and femoral neck (FIG. 6B) after a 6-week treatment with HBD1 (3-11) with C18:0 at N-terminal in OVX Sprague-Dawley rats (*: p-value<0.05, vs OVX vehicle).
Figure 6B:
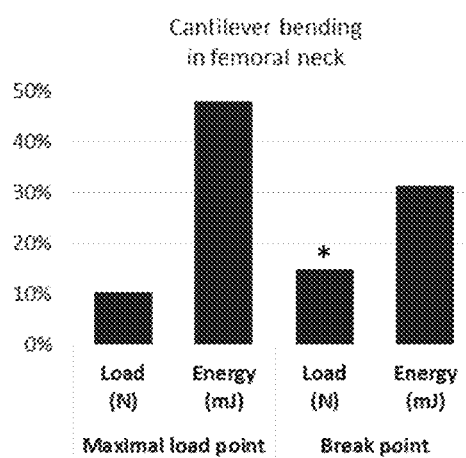

Bone biomechanical properties were determined by compression test using Instron 3343 biomechanical testing system (Instron, Norwood, Mass., USA). The biomechanical tests were performed ex vivo in a lumbar vertebrae (compression test) and in femoral neck (cantilever bending test) at the end of the treatment period. FIG. 6A shows the percent increase from OVX animals in group treated with high dose of HBD1 (3-11) with stearic acid at the N-terminus (C18:0) in compression test in lumbar vertebral body for following selected parameters: Maximal load (N), Energy absorption at maximal load (mJ) and Stress at maximal load (MPa). FIG. 6B illustrates the percent increase from OVX animals in group treated with high dose of HBD1 (3-11) with stearic acid at the N-terminus (C18:0) in cantilever bending test in femoral neck for following selected parameters: Load (N) and Energy (mJ) at maximal load point; Load (N) and Energy (mJ) at break point.

The results show that HBD1 (3-11) with stearic acid at the N-terminus (C18:0) has anabolic effect on bone in ovariectomized rat. In particular, it increased percent bone volume fraction (BV/TV), trabecular number (Tb.N) and connectivity density (Conn.D) at tibial metaphysis in a dose-dependent manner as presented in FIGS. 5A, 5B and 5C. In addition, 3.2 mg/kg BID dose of HBD1 (3-11) with stearic acid at the N-terminus (C18:0) increased bone strength as indicated by improved biomechanical properties (in particular maximal load, energy absorption at maximal load and stress at maximal load) of lumar vertebrae and of femoral neck (in particular load at break point) as presented in FIGS. 6A and 6B.

In conclusion, HBD1 (3-11) with stearic acid at the N-terminus (C18:0) and the peptides of the present disclosure may induce bone formation. This may imply a therapeutic potential in a number of bone-related disorders, including osteoporosis, osteogenesis imperfecta, and other disorders associated with impaired bone metabolism.

It is understood that the data reported in the present specification are only given to illustrate the present disclosure and may not be regarded as constituting a limitation thereof.

While the present disclosure has been described in connection with specific embodiments thereof, it will be understood that it is capable of further modifications and this application is intended to cover any variations, uses, or adaptations of the present disclosure following, in general, the principles of the present disclosure and including such departures from the present disclosure as come within known or customary practice within the art to which the present disclosure pertains and as may be applied to the essential features hereinbefore set forth, and as follows in the scope of the appended claims.

All published documents mentioned in the present specification are herein incorporated by reference.

BIBLIOGRAPHY

WO 2005/014635;
U.S. Pat. No. 9,220,746;
Xi G. et al. The Heparin-Binding Domains of IGFBP-2 Mediate Its Inhibitory Effect on Preadipocyte Differentiation and Fat Development in Male Mice. *Endocrinology,* 154(11):4146-4157 (2013).
Poster 0268 by Xi et al. presented at the Annual Meeting of the American Society for Bone and Mineral Research (ASBMR) in Atlanta on Sep. 16-19, 2016. A unique peptide containing the heparin binding domain of IGFBP-2 increases bone mass in ovariectomized (OVX) rats.
Wheatcroft S B, Kearney M T, Shah A M, Ezzat V A, Miell J R, Modo M, Williams S C, Cawthorn W P, Medina-Gomez G, Vidal-Puig A, Sethi J K, Crossey P A. IGF-binding protein-2 protects against the development of obesity and insulin resistance. Diabetes. 2007; 56(2): 285-294.
DeMambro V E, Clemmons D R, Horton L G, et al. Gender-specific changes in bone turnover and skeletal architecture in igfbp-2-null mice. Endocrinology. 2008; 149(5):2051-2061.
Hedbacker K, Birsoy K, Wysocki R W, et al. Antidiabetic effects of IGFBP2, a leptin-regulated gene. Cell Metab. 2010; 11(1):11-22.
Xi, G. et al. (2014) IGFBP-2 directly stimulates osteoblast differentiation. J. Bone Miner. Res. 20, 2427-2438
Kawai M, Breggia A C, DeMambro V E, et al. The heparin binding domain of IGFBP-2 has insulin-like growth factor binding-independent biologic activity in the growing skeleton. J Biol Chem. 2011; 286(16): 14670-80.

The invention claimed is:

1. An isolated peptide consisting of a heparin binding domain (HBD) fragment as set forth in SEQ ID NO: 73.

2. A composition comprising the isolated peptide of claim 1 together with a suitable pharmaceutical excipient.

3. A method for treatment of a bone disorder in a subject in need thereof, the method comprising administering the isolated peptide of claim 1 to the subject in an amount effective to treat the bone disorder in the subject.

4. The method of claim 3, wherein the bone disorder is selected from: osteoporosis, osteopenia, osteogenesis imperfecta, osteonecrosis, low bone mass, Paget's disease of bone, aseptic prosthetic loosening, metastatic bone disease, rheumatoid arthritis, lupus arthritis, periodontal disease, alveolar bone loss, post-osteotomy, childhood idiopathic bone loss, curvature of the spine, loss of height, and prosthetic surgery.

5. The method of claim 4, wherein the bone disorder is selected from: a broken bone, a bone defect, a bone transplant, a bone graft, a bone cancer, a joint replacement, a joint repair, a fusion, a facet repair, a bone degeneration, a dental implant, a dental repair, and any combination thereof.

6. The method of claim 3, wherein the effective amount is from about 1 µg/kg to about 50 mg/kg.

7. The method of claim 3, wherein said administering is continued for a period of at least about 10 weeks or about 24 weeks.

* * * * *

UNITED STATES PATENT AND TRADEMARK OFFICE
CERTIFICATE OF CORRECTION

PATENT NO. : 10,947,285 B2
APPLICATION NO. : 15/888402
DATED : March 16, 2021
INVENTOR(S) : David Clemmons et al.

Page 1 of 3

It is certified that error appears in the above-identified patent and that said Letters Patent is hereby corrected as shown below:

On the Title Page

In Column 1, item (72), Inventors, Line 4, delete "Lyons" and insert -- Lyon --.

On page 2, in Column 1, item (56), Other Publications, Line 16, delete "bisease." and insert -- Disease. --.

On page 2, in Column 2, item (56), Other Publications, Line 1, delete "1 st colurnn, 1 st" and insert -- 1st column, 1st --.

On page 2, in Column 2, item (56), Other Publications, Line 2, delete "1 st" and insert -- 1st --.

In the Specification

In Column 7, Line 30 (approx.), table 1, delete "$^1$____GLEEPKK__-$^{13}$" and insert -- $^1$-____GLEEPKK__-$^{13}$ --.

In Column 7, Line 35 (approx.), table 1, delete "$^{cyclic1}$-HLGLEEPKK-$^{13cyc1c}$" and insert -- $^{cyclic1}$-HLGLEEPKK-$^{13cyclic}$ --.

In Column 7, Line 36 (approx.), table 1, after "(5-9)" and insert -- $^1$-___GLEEP___-$^{13}$ --.

In Column 9, Line 46 (approx.), delete "pyrroly sine" and insert -- pyrrolysine --.

In Column 12, Line 28 (approx.), table 4, delete "HBD 1" and insert -- HBD1 --.

In Column 14, Line 36 (approx.), delete "tridecyclic" and insert -- tridecylic --.

In Column 21, Line 45, delete "humerous" and insert -- humerus --.

Signed and Sealed this
Sixth Day of July, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,947,285 B2

Page 2 of 3

In Column 23, Line 57 (approx.), table 9, delete "SD" and insert -- SE --.

In Column 24, Line 6 (approx.), table 9, delete "SD" and insert -- SE --.

In Column 24, Line 8 (approx.), table 9, delete "+" and insert -- ± --.

In Column 24, Line 10 (approx.), table 9, delete "+" and insert -- ± --.

In Column 24, Line 12 (approx.), table 9, delete "+" and insert -- ± --.

In Column 25, Line 7 (approx.), table 10, after "Dose" insert -- (µg/mL) --.

In Column 25, Line 58, delete "examined" and insert -- examined. --.

In Column 25, Line 63, delete "activity" and insert -- activity. --.

In Column 26, Line 57, delete "µmon)." and insert -- µmol/L). --.

In Column 27, Line 3, delete "examined" and insert -- examined. --.

In Column 27, Line 57, delete "12)" and insert -- 12). --.

In Column 28, Line 8 (approx.), delete "HBD 1" and insert -- HBD1 --.

In Column 29, Line 41 (approx.), table 14, delete "SE" and insert -- SD --.

In Column 29, Line 62 (approx.), table 14, delete "HLGLEEPEQ" and insert -- HLGLEEPFQ --.

In Column 30, Line 7 (approx.), table 14, delete "SE" and insert -- SD --.

In Column 30, Line 14 (approx.), delete "examined" and insert -- examined. --.

In Column 30, Line 27 (approx.), table 15, delete "SE" and insert -- SD --.

In Column 30, Line 54 (approx.), delete "(3-11)" and insert -- (3-11). --.

In Column 30, Line 62 (approx.), table 16, delete "SE" and insert -- SD --.

In Column 31, Line 7 (approx.), table 16, delete "SE" and insert -- SD --.

In Column 31, Line 43, delete "polyethersulfane" and insert -- polyethersulfone --.

In Column 32, Lines 7-8, delete "PolyEthyleneGlycol" and insert -- Polyethylene Glycol --.

In Column 32, Line 25 (approx.), table 17, delete "DM±SE" and insert -- SEQ ID NO: 1 ±SE --.

CERTIFICATE OF CORRECTION (continued)
U.S. Pat. No. 10,947,285 B2

In Column 33, Line 30, table 18, delete "Ccontrol" and insert -- Control --.

In Column 34, Line 47 (approx.), table 19, delete "SE" and insert -- SD --.

In Column 34, Line 63 (approx.), table 20, delete "SE" and insert -- SD --.

In Column 35, Line 6 (approx.), table 20, delete "SE" and insert -- SD --.

In Column 35, Line 23 (approx.), table 21, delete "SE" and insert -- SD --.

In Column 35, Line 44, delete "(C16:0))" and insert -- (C16:0) --.

In Column 35, Line 61, delete "(C16:0))" and insert -- (C16:0) --.

In Column 38, Line 20, delete "HBD-1" and insert -- HBD1 --.

In Column 39, Line 9 (approx.), table 24, delete "HBD-1" and insert -- HBD1 --.

In Column 39, Line 34, delete "albumin)" and insert -- albumin). --.

In Column 40, Line 44, delete "(AUC$_{0-4}$)" and insert -- (AUC$_{0-t}$) --.

In Column 41, Line 23, delete "Sky Scan" and insert -- SkyScan --.

In Column 42, Line 1, delete "lumar" and insert -- lumbar --.